(12) United States Patent
Gharib et al.

(10) Patent No.: US 11,653,894 B2
(45) Date of Patent: May 23, 2023

(54) SYSTEM AND METHODS FOR NERVE MONITORING

(71) Applicant: NuVasive, Inc., San Diego, CA (US)

(72) Inventors: James E. Gharib, San Diego, CA (US); Albert Pothier, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 100 days.

(21) Appl. No.: 16/384,936

(22) Filed: Apr. 16, 2019

(65) Prior Publication Data

US 2019/0307418 A1    Oct. 10, 2019

Related U.S. Application Data

(63) Continuation of application No. 14/881,091, filed on Oct. 12, 2015, now Pat. No. 10,299,756, which is a (Continued)

(51) Int. Cl.
*A61B 8/08*   (2006.01)
*A61B 5/00*   (2006.01)
(Continued)

(52) U.S. Cl.
CPC .............. *A61B 8/085* (2013.01); *A61B 5/24* (2021.01); *A61B 5/389* (2021.01); *A61B 5/4893* (2013.01); *A61B 8/0875* (2013.01); *A61B 8/12* (2013.01); *A61B 8/14* (2013.01); *A61B 8/445* (2013.01); *A61B 8/4483* (2013.01); *A61B 8/4488* (2013.01); *A61B 8/463* (2013.01); *A61B 17/0206* (2013.01); *A61B 8/0833* (2013.01); *A61B 8/0841* (2013.01); *A61B 8/4494* (2013.01); *A61B 17/1671* (2013.01); *A61B 17/1703* (2013.01); *A61B 17/1757* (2013.01);
(Continued)

(58) Field of Classification Search
CPC ......... A61B 8/085; A61B 8/0875; A61B 8/12; A61B 8/14; A61B 8/445; A61B 8/4483; A61B 5/04001; A61B 5/0488; A61B 5/4893
See application file for complete search history.

(56) References Cited

U.S. PATENT DOCUMENTS

| 972,983 A | 10/1910 | Arthur |
| 1,328,624 A | 1/1920 | Graham |

(Continued)

FOREIGN PATENT DOCUMENTS

| DE | 299 08 259 | 7/1999 |
| EP | 0 759 307 | 2/1997 |

(Continued)

OTHER PUBLICATIONS

"Electromyography System," International Search report from International Application No. PCT/US00/32329, dated Apr. 27, 2001, 9 pages.

(Continued)

*Primary Examiner* — Patricia J Park
(74) *Attorney, Agent, or Firm* — Seager, Tufte & Wickhem, LLP

(57) ABSTRACT

A system and related methods for performing nerve detection during surgical access using ultrasound testing during surgery.

15 Claims, 23 Drawing Sheets

Related U.S. Application Data continuation of application No. 14/063,184, filed on Oct. 25, 2013, now abandoned, which is a continuation of application No. 11/528,981, filed on Sep. 27, 2006, now Pat. No. 8,568,317.

(60) Provisional application No. 60/721,425, filed on Sep. 27, 2005.

(51) Int. Cl.
| | |
|---|---|
| A61B 8/12 | (2006.01) |
| A61B 8/00 | (2006.01) |
| A61B 17/02 | (2006.01) |
| A61B 5/24 | (2021.01) |
| A61B 5/389 | (2021.01) |
| A61B 8/14 | (2006.01) |
| A61B 17/16 | (2006.01) |
| A61B 17/17 | (2006.01) |
| A61B 17/70 | (2006.01) |
| A61B 17/00 | (2006.01) |

(52) U.S. Cl.
CPC ..... A61B 17/70 (2013.01); A61B 2017/00039 (2013.01); A61B 2017/0262 (2013.01)

(56) References Cited

U.S. PATENT DOCUMENTS

| | | |
|---|---|---|
| 1,548,184 A | 8/1925 | Cameron |
| 2,704,064 A | 6/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,938,502 A | 2/1976 | Bom |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 9/1986 | Rantala |
| 4,616,660 A | 10/1986 | Johns |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,078,147 A | 1/1992 | Reid |
| 5,081,990 A | 1/1992 | Deletis |
| 5,092,344 A | 3/1992 | Lee |
| 5,125,406 A | 6/1992 | Goldstone et al. |
| 5,127,403 A | 7/1992 | Brownlee |
| 5,161,533 A | 11/1992 | Prass et al. |
| 5,196,015 A | 3/1993 | Neubardt |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,248 A | 10/1996 | Matthews |
| 5,579,781 A | 12/1996 | Cooke |
| 5,593,429 A | 1/1997 | Ruff |
| 5,599,279 A | 2/1997 | Slotman et al. |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,779,642 A | 4/1998 | Nightengale |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,785,656 A | 7/1998 | Chiabrera et al. |
| 5,785,658 A | 7/1998 | Benaron |
| 5,797,397 A | 8/1998 | Rosenberg |
| 5,797,854 A | 8/1998 | Hedgecock |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,976,094 A | 11/1999 | Gozani et al. |
| 6,004,262 A | 12/1999 | Putz et al. |
| 6,011,985 A | 1/2000 | Athan et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Turner et al. |
| 6,139,493 A | 10/2000 | Koros et al. |
| 6,139,545 A | 10/2000 | Utley |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |

(56) References Cited

U.S. PATENT DOCUMENTS

| | | |
|---|---|---|
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,348,058 B1 | 2/2002 | Melkent et al. |
| 6,393,325 B1 | 5/2002 | Mann et al. |
| 6,425,859 B1 | 7/2002 | Foley et al. |
| 6,425,901 B1 | 7/2002 | Zhu et al. |
| 6,451,015 B1 | 9/2002 | Rittman, III et al. |
| 6,457,365 B1 | 10/2002 | Stephens et al. |
| 6,466,817 B1 | 10/2002 | Kaula et al. |
| 6,500,128 B2 | 12/2002 | Marino |
| 6,507,755 B1 | 1/2003 | Turner et al. |
| 6,508,769 B2 | 1/2003 | Bonnefous |
| 6,535,759 B1 | 3/2003 | Epstein et al. |
| 6,564,078 B1 | 5/2003 | Marino et al. |
| 6,579,244 B2 | 6/2003 | Goodwin |
| 6,582,441 B1 | 6/2003 | He et al. |
| 6,585,638 B1 | 7/2003 | Yamamoto |
| 6,618,626 B2 | 9/2003 | West et al. |
| 6,719,692 B2 | 4/2004 | Kleffner et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,902,569 B2 | 6/2005 | Parmer et al. |
| 6,926,728 B2 | 8/2005 | Zucherman et al. |
| 6,929,606 B2 | 8/2005 | Ritland |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,207,949 B2 | 4/2007 | Miles et al. |
| 7,258,688 B1 | 8/2007 | Shah et al. |
| 7,294,127 B2 | 11/2007 | Leung et al. |
| 7,310,546 B2 | 12/2007 | Prass |
| 7,517,318 B2 | 4/2009 | Altmann et al. |
| 2001/0031921 A1 | 10/2001 | Bonnefous |
| 2001/0036245 A1 | 11/2001 | Kienzle et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0013529 A1 | 1/2002 | Smith et al. |
| 2002/0032462 A1* | 3/2002 | Houser ............... A61B 17/11 606/213 |
| 2002/0072686 A1 | 6/2002 | Hoey et al. |
| 2002/0103428 A1 | 8/2002 | DeCharms |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0078618 A1 | 4/2003 | Fey et al. |
| 2003/0105503 A1 | 6/2003 | Marino |
| 2003/0135112 A1* | 7/2003 | Ritter ................ A61B 5/06 600/424 |
| 2004/0059328 A1 | 3/2004 | Daniel et al. |
| 2004/0092821 A1* | 5/2004 | Hering ............... A61B 8/12 600/459 |
| 2004/0152972 A1 | 8/2004 | Hunter |
| 2004/0199084 A1 | 10/2004 | Kelleher et al. |
| 2004/0215071 A1 | 10/2004 | Frank et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0070913 A1* | 3/2005 | Milbocker ......... A61B 17/1671 606/92 |
| 2005/0075578 A1 | 4/2005 | Gharib et al. |
| 2005/0080418 A1 | 4/2005 | Simonson et al. |
| 2005/0119660 A1 | 6/2005 | Burlion |
| 2005/0159817 A1* | 7/2005 | Ferree ................ A61B 17/15 623/17.11 |
| 2005/0182454 A1 | 8/2005 | Gharib et al. |
| 2005/0240126 A1* | 10/2005 | Foley ................. A61B 8/06 601/2 |
| 2005/0256582 A1 | 11/2005 | Feree |
| 2005/0283148 A1* | 12/2005 | Janssen ............... A61B 90/30 606/34 |
| 2005/0285858 A1* | 12/2005 | Yang ................ G06T 15/08 345/420 |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0085049 A1* | 4/2006 | Cory ................ A61B 5/0536 607/48 |
| 2006/0089609 A1 | 4/2006 | Bleich et al. |
| 2006/0224078 A1 | 10/2006 | Hoey et al. |
| 2007/0016097 A1 | 1/2007 | Farquhar et al. |
| 2007/0066887 A1* | 3/2007 | Mire ................ A61B 34/20 600/424 |
| 2007/0198062 A1 | 8/2007 | Miles et al. |
| 2007/0293782 A1 | 12/2007 | Marino |
| 2008/0015612 A1 | 1/2008 | Urmey |
| 2008/0039914 A1 | 2/2008 | Cory et al. |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0119737 A1 | 5/2008 | Urbano et al. |

FOREIGN PATENT DOCUMENTS

| | | |
|---|---|---|
| EP | 0 972 538 | 1/2000 |
| FR | 2 795 624 | 1/2001 |
| FR | 2 796 846 | 2/2001 |
| JP | 408057014 | 3/1996 |
| WO | 00/38574 | 7/2000 |
| WO | 00/66217 | 11/2000 |
| WO | 00/67645 | 11/2000 |
| WO | 01/03604 | 1/2001 |
| WO | 01/37728 | 5/2001 |
| WO | 03/005887 | 1/2003 |
| WO | 03/026482 | 4/2003 |
| WO | 03/037170 | 5/2003 |
| WO | 04/012809 | 2/2004 |
| WO | 04/064634 | 8/2004 |
| WO | 05/013805 | 2/2005 |
| WO | 06/042075 | 4/2006 |
| WO | 06/084193 | 8/2006 |

OTHER PUBLICATIONS

"Nerve Proximity and Status Detection System and Method," International Search Report from International Application No. PCT/US01/18606, dated Oct. 18, 2001, 6 pages.

"Relative Nerve Movement and Status Detection System and Method," International Search Report from International Application No. PCT/US01/18579, dated Jan. 15, 2002, 6 pages.

"System and Method for Determining Nerve Proximity Direction and Pathology During Surgery," International Search Report from International Application No. PCT/US02/22247, dated Mar. 27, 2003, 4 pages.

"System and Methods for Determining Nerve Direction to a Surgical Instrument," International Search Report from International Application No. PCT/US03/02056, dated Aug. 12, 2003, 5 pages.

"Systems and Methods for Performing Percutaneous Pedicle Integrity Assessments," International Search Report from International Application No. PCT/US02/35047, dated Aug. 11, 2003, 5 pages.

"Systems and Methods for Performing Surgery Procedures and Assessments," International Search Report from International Application No. PCT/US02/30617, dated Jun. 5, 2003, 4 pages.

"Systems and Methods for Performing Neurophysiologic Assessments During Spine Surgery," International Search Report from International Application No. PCT/US06/03966, dated Oct. 23, 2006, 5 pages.

(56) References Cited

OTHER PUBLICATIONS

"Multi-Channel Stimulation Threshold Detection Algorithm for Use in Neurophysiology Monitoring," International Search Report from International Application No. PCT/US06/37013, dated Mar. 19, 2007, 10 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor," RLN Systems Inc. Operator's Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, 2002, 27(14): 1577-1581.
Bose et al., "Neurophysiologic Monitoring of Spinal Nerve Root Function During Instrumented Posterior Lumber Spine Surgery," *Spine*, 2002, 27(13): 1444-1450.
Calancie et al., "Stimulus-Evoked EMG Monitoring During Transpedicular Lumbosacral Spine Instrumentation," *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al., "The Use of Evoked EMG in Detecting Misplaced Thoracolumbar Pedicle Screws," *Spine*, 2001, 26(12): 1313-1316.
Darden et al., "A Comparison of Impedance and Electromyogram Measurements in Detecting the Presence of Pedicle Wall Breakthrough," *Spine*, 1998, 23(2): 256-262.
Ebraheim et al., "Anatomic Relations Between the Lumbar Pedicle and the Adjacent Neural Structures," *Spine*, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia and Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, 1983, 129: 637-642.
Minahan et al., "The Effect of Neuro muscular Blockade on Pedicle Screw Stimulation Thresholds," *Spine*, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach," *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4): 1-6.
Raj et al., "Use of the Nerve Stimulator for Peripheral Blocks," *Regional Anesthesia*, 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Moed et al., "Insertion of an iliosacral implant in an animal model," *Journal of Bone and Joint Surgery*, 1999, 81A(11): 1529-1537.
"NIM-Response, so advanced...yet so simple," XoMed, Inc., 1999, 12 pages.
Moed et al., "Intraoperative monitoring with stimulus-evoked electromyography during placement of iliosacral screws," *The Journal of Bone and Joint Surgery*, 1998, 81A(4): 10 pages.
"New data analyzer combines the functions of six instruments in one unit," News Release, Nov. 11, 1987, 3 pages.
"NuVasive's spine surgery system cleared in the US," *Pharm & Medical Industry Week*, Dec. 10, 2001, 1 page.
"Risk Capital Funds," *Innovation*, Mar. 6, 1990, 172: 3 pages.
Bednarik et al., "The Value of Somatosensory-and Motor-Evoked Potentials in Predicting and Monitoring the Effect of Therapy in Spondylotic Cervical Myelopathy: Prospective Randomized Study," *Spine*, 1999, 24(15): 1593-1598.
Calancie et al., "'Threshold-level' multipulse transcranial electrical stimulation of motor cortex for intraoperative monitoring of spinal motor tracts: description of method and comparison to somatosensory evoked potential monitoring." *Journal of Neurosurgery*, 1998, 88:457-470.
Calancie et al., "Threshold-level repetitive transcranial electrical stimulation for intraoperative monitoring of central motor conduction," *Journal of Neurosurgery (Spine 1)*, 2001, 95: 161-168.
Calancie et al., "Alarm Criteria for Motor-Evoked Potentials: What's Wrong with the 'Presence-or-Absence' Approach?," *Spine*, 2008, 33(4): 406-414.
Deletis et al., "Neurophysiological mechanisms underlying motor evoked potentials in anesthetized humans. Part 2: Relationship between epidurally and muscle recorded MEPs in Man," *Clinical Neurophysiology*, 2001, 112: 445-452.
Deletis et al., "Neurophysiological mechanisms underlying motor evoked potentials in anesthetized humans. Part 1: Recovery time of corticospinal tract direct waives elicited by pairs of transcranial electrical stimuli," *Clinical Neurophysiology*, 2001, 112: 438-444.
Ginsberg et al., "Postoperative paraplegia with preserved intraoperative somatosensory evoked potentials: Case report," *Journal of Neurosurgery*, 1985, 63: 296-300.
Gokaslan et al., "Intraoperative Monitoring of Spinal Cord Function Using Motor Evoked Potentials via Transcutaneous Epidural Electrode During Anterior Cervical Spinal Surgery," *Journal of Spinal Disorders*, 1997, 10(4): 299-303.
Kombos et al., "Monitoring of intraoperative motor evoked potentials to increase the safety of surgery in and around the motor cortex," *Journal of Neurosurgery*, 2001, 95:608-614.
Langeloo et al., "A New Application of TCE-MEP: Spinal Cord Monitoring in Patients With Severe Neuromuscular Weakness Undergoing Corrective Spine Surgery," *Journal of Spinal Disorders*, 2001, 14(5): 445-448.
Langeloo et al., "Transcranial Electrical Motor-Evoked Potential Monitoring During Surgery for Spinal Deformity: A Study of 145 Patients," Spine, 2003, 28(10): 1043-1050.
MacDonald, "Safety of Intraoperative Transcranial Electric Stimulation Motor Evoked Potential Monitoring," *Journal of Clinical Neurophysiology*, 2002, 19(5): 416-429.

(56) References Cited

OTHER PUBLICATIONS

Osburn et al., "TCeMEPs offer Safe, Reliable Monitoring of Spinal Cord Motor Pathway Function during Cervical Procedures Performed for Post-traumatic Spine Injury," 2 pages.

Osburn, "A Guide to the Performance of Transcranial Electrical Motor Evoked Potentials. Part 1. Basic Concepts, Recording Parameters, Special Considerations, and Application," *American Journal of Electroneurodiagnosic Technology*, 2006, 46: 98-158.

Watanabe et al., "Transcranial electrical stimulation through screw electrodes for intraoperative monitoring of motor evoked potentials: Technical note." *Journal of Neurosurgery*, 2004, 100: 155-160.

Wiedemayer et al., "False negative findings in intraoperative SEP monitoring: analysis of 658 consecutive neurosurgical cases and review of published reports," *Journal of Neurology, Neurosurgery, and Psychiatry*, 2004, 75: 280-286.

Balzer et al., "Simultaneous Somatosensory Evoked Potential and Electromyographic Recordings in Lumbosacral Decompression and Instrumentation Technique Application," *Neurosurgery*, 1998 42:1318-1325.

Banoczi, "Update on Anesthetic and Metabolic Effects During Intraoperative Neurophysiological Monitoring (IONM)," *American Journal of Electroneurodiagnostic Technology*, 2005, 45: 225-239.

Chawla et al., "Somatosensory Evoked Potentials: Clinical Applications," http://emedicine.medscape.com/article/1139393-overview, 6 pages.

Dawson et al., "Spinal Cord Monitoring: Results of the Scoliosis Research Society and the European Spinal Deformity Society Survey," *Spine*, 1991 16(8 Supplement): S361-S364.

Deutsch et al., "Somatosensory evoked potential monitoring in anterior thoracic vertebrectomy," *Journal of Neurosurgery (Spine 2)*, 2000, 92:155-161.

Devlin et al., "Intraoperative Neurophysiologic Monitoring During Spinal Surgery," *Journal of the American Academy of Orthopedic Surgeons*, 2007, 15(9): 549-560.

Gunnarsson et al., "Real-Time Continuous Intraoperative Electromyographic and Somatosensory Evoked Potential Recordings in Spinal Surgery: Correlation of Clinical and Electrophysiologic Findings in a Prospective, Consecutive Series of 213 Cases," *Spine*, 2004, 29(6): 677-684.

Jones et al., "Two cases of quadriparesis following anterior cervical discectomy, with normal perioperative somatosensory evoked potentials," *Journal of Neurology, Neurosurgery, and Psychiatry*, 2003, 74: 273-276.

Kamel et al., "The Use of Somatosensory Evoked Potentials to Determine the relationship Between Patient Positioning and Impending Upper Extremity Nerve Injury During Spine Surgery: A Retrospective Analysis," *Anesthesia and Analgesia*, 2006, 102:1538-1542.

Kombos et al., "Impact of Somatosensory Evoked Potential monitoring on Cervical Surgery," *Journal of Clinical Neurophysiology*, 2003, 20(2): 122-128.

Kraft et al., "Somatosensory Evoked Potentials: Clinical Uses," *Muscle Nerve*, 1998, 21: 252-258.

Legatt et al., "Somatosensory Evoked Potentials: General Principles," http://emedicine.medscape.com/article/1139906-overview, 2006, 11 pages.

More et al., "Cortical Evoked Potential Monitoring During Spinal Surgery: Sensitivity, Specificity, Reliability, and Criteria for Alarm," *Journal of Spinal Disorders*, 1988, 1(1): 75-80.

Nash et al., "Spinal Cord Monitoring During Operative Treatment of the Spine," *Clinical Orthopedics and Related Research*, 1977, 126:100-105.

Nuwer et al., "Somatosensory evoked potential spinal cord monitoring reduces neurologic deficits after scoliosis surgery: results of a large multicenter survey," *Electroencephalography and Clinical Neurophysiology*, 1995, 96: 6-11.

Padberg et al., "Somatosensory- and Motor-Evoked Potential Monitoring Without a Wake-Up Test During Idiopathic Scoliosis Surgery: An Accepted Standard of Care," *Spine*, 1998, 23(12): 1392-1400.

Pelosi et al., "Combined monitoring of motor and somatosensory evoked potentials in orthopaedic spinal surgery," Clinical Neurophysiology, 2002, 113: 1082-1091.

Sloan, "Anesthesia for Intraoperative Neurophysiologic Monitoring of the Spinal Cord," *Journal of Clinical Neurophysiology*, 2002, 19(5): 430-443.

Toleikis, "Intraoperative Monitoring Using Somatosensory Evoked Potentials: A Position Statement by the American Society of Neurophysiological Monitoring," *Journal of Clinical Monitoring and Computing*, 2005, 19: 241-258.

Wiedemayer et al., "The impact of neurophysiological intraoperative monitoring on surgical decisions: A critical analysis of 423 cases," *Journal of Neurosurgery*, 2002, 96: 255-262.

Zornow et al., "Case Report: Intraoperative Somatosensory Evoked Responses Recorded during Onset of the Anterior Spinal Artery Syndrome," 369, 1989, 5(4): 243-245.

* cited by examiner

SYSTEM AND METHODS FOR NERVE MONITORING

CROSS REFERENCE TO RELATED APPLICATIONS

This application is a continuation U.S. patent application Ser. No. 14/881,091 filed Oct. 12, 2015, which is a continuation of U.S. patent application Ser. No. 14/063,184 filed Oct. 25, 2013, now abandoned, which is a continuation of U.S. patent application Ser. No. 11/528,981 filed Sep. 27, 2006 (now U.S. Pat. No. 8,568,317), which claims priority to U.S. Provisional Patent Application No. 60/721,425 filed Sep. 27, 2005, the entire contents of which are hereby expressly incorporated by reference into this disclosure as if set forth in its entirety herein.

BACKGROUND OF THE INVENTION

Field

The present invention relates generally to a system and related methods for performing at least one of bone integrity testing and nerve detection during surgical access using both neurophysiologic testing and ultrasound testing during surgery.

Discussion

It has been estimated that somewhere between 50 and 70 million people suffer from chronic back pain in the United States. In most cases, conservative therapies, including, for example, bed rest and physical therapy will succeed in alleviating, or at least significantly reducing the back pain. Still, a significant number of patients are unaided by conservative therapies alone and undergo spinal surgery before finding relief. The rate at which caregivers and patients opt for surgery also continues to grow as medical technology advances and surgical options increase. In all, approximately 750,000 spine surgeries are performed per year in the United States alone.

When necessary, spine surgery may provide great benefit to the patient, often allowing patients to resume activities long since abandoned because of the debilitating pain. Spine surgery, however, is not without risk. Operating on or near the spine generally means operating in close proximity to delicate neural tissue, such as the spinal cord and nerve roots. Damage to the neural tissue, which may be caused (for example) by inadvertent contact with a surgical instrument and/or implant while accessing the spinal target site or inadvertent contact of an implant or surgical instrument and/or implant before or during pedicle screw placement. One way to mitigate this risk is to conduct neurophysiologic monitoring during the procedure and/or recovery period. Neurophysiologic monitoring generally consists of stimulating neural tissue and analyzing responses (generally electrical waveforms) generated by the stimulus. While such neurophysiologic monitoring has proved an exceedingly valuable tool in efforts to prevent neurological damage during spine surgery there is still room for further improvements. The present invention is directed at such an improvement.

SUMMARY OF THE INVENTION

According to a broad aspect, the present invention includes a surgical system, comprising a surgical instrument having at least one stimulation electrode for transmitting a stimulation signal for performing neurophysiologic testing during surgery and/or at least one transducer for transmitting and/or receiving signals for performing ultrasound-based testing during surgery. The testing may include, but is not necessarily limited to, pedicle integrity testing associated with the use of pedicle screws (e.g. hole formation, preparation, and screw placement) and surgical access.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
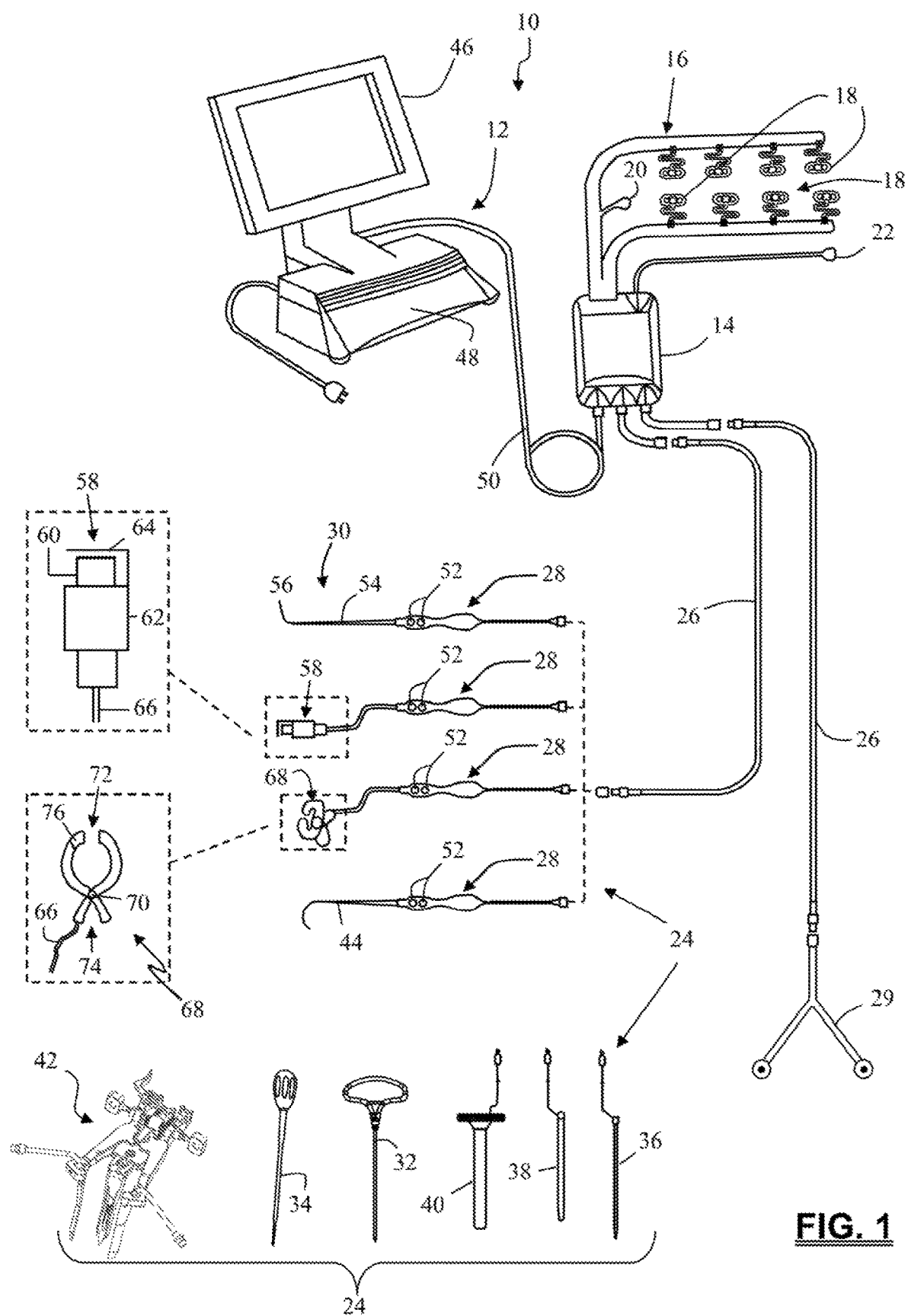
FIG. 1 is a perspective view of an exemplary surgical system 10 capable of neurophysiologic assessments together with ultrasound monitoring to aimed to safely access the spine and properly implant pedicle screws for fixation.

The present invention is directed towards enabling safe and reproducible spinal surgery by aiding in, among other things, access to a target site in the spine (including but not necessarily limited to a pedicle) and pedicle screw implantation (including but not necessarily limited to formation and preparation of pilot holes and screw placement). To do so the present invention integrates a host of imaging and neurophysiologic assessment capabilities together in a single, user-friendly and surgeon directed system. FIG. 1 illustrates, by way of example only, a surgical system 10 capable carrying neurophysiologic assessment functions including, but not necessarily limited to, Basic, Difference, and Dynamic Screw Tests (pedicle integrity testing), Detection (nerve proximity testing during surgical access) and Free Run EMG (detection of spontaneous muscle activity, may be conducted in any mode). Simultaneously, the surgical system 10 is capable of performing ultrasound imaging to aid in intraoperative guidance of surgical instrumentation through bone, and in particular, through the cancellous bone forming the interior region of the pedicle as well as enhancing nerve detection. It is expressly noted that, although described herein largely in terms of use in spinal surgery, the surgical system 10 and related methods of the present invention are suitable for use in any number of additional surgical procedures where neurological impairment is a concern.

The neuromonitoring system 10 includes a control unit 12, a patient module 14, an EMG harness 16, including eight pairs of EMG electrodes 18 and a return electrode 22 coupled to the patient module 14, and one or more of a host of surgical accessories 24 capable of being coupled to the patient module 14 (preferably via a stimulation handpiece 28 and accessory cables 26), and a pair of peripheral nerve stimulation (PNS) electrodes (one positive and one negative) 29 also coupled to the patient module 14. The surgical accessories 24 may include, but are not necessarily limited to, devices for performing pedicle screw tests (such as a screw test probe 30, tap member 32, bone awl 34), surgical access components (such as a K-wire 36, one or more dilating cannula 38, 40, a tissue retractor assembly 42), and neural pathology monitoring devices (such as a nerve root retractors 44, 45), any of which may also be fitted with one or more ultrasound transducers 55 for imaging of surrounding tissue during use. The neuromonitoring system 10 accomplishes neuromonitoring by having the control unit 12 and patient module 14 cooperate to send stimulation signals to one or more stimulation electrodes or electrode regions on the various surgical accessories, while sensors detect muscle activity caused by the stimulation signal.

Figure 2:
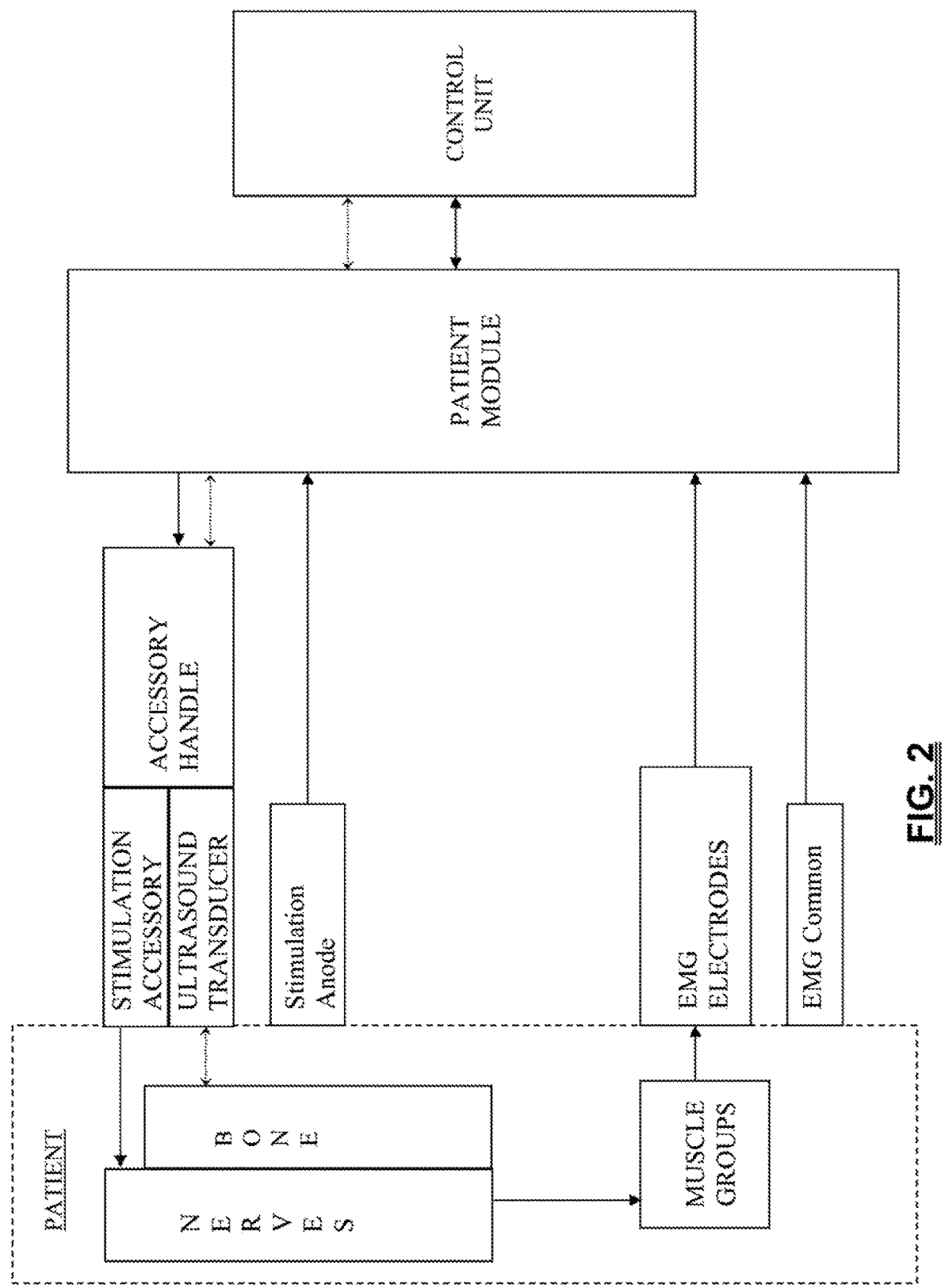
FIG. 2 is a block diagram of the surgical system 20 shown in FIG. 1.

A block diagram of the neuromonitoring system 10 is shown in FIG. 2, the operation of which is readily apparent in view of the following description. The control unit 12 includes a touch screen display 46 and a base 48, which collectively contain the essential processing capabilities for controlling the neuromonitoring system 10. The touch screen display 26 is preferably equipped with a graphical user interface (GUI) capable of communicating information to the user and receiving instructions from the user. The base 48 contains computer hardware and software that commands the stimulation and ultrasound sources, receives digitized signals and other information from the patient module 14, processes EMG responses, performs ultrasound image processing, and displays the processed data to the operator via the display 46. The primary functions of the software within the control unit 12 include receiving user commands via the touch screen display 46, activating stimulation in the requested mode (Basic Screw Test, Difference Screw Test, Dynamic Screw Test, MaXcess Detection), processing EMG signal data according to defined algorithms, activating ultrasound signaling, processing ultrasound signal data into viewable images, displaying received parameters and processed data, and monitoring system status.

The patient module 14 is connected via a data cable 50 (or optionally via wireless communication) to the control unit 12, and contains the electrical connections to all electrodes, EMG signal conditioning circuitry, stimulator drive and steering circuitry, ultrasound signal conditioning and receiving circuitry and a digital communications interface to the control unit 12. In use, the control unit 12 is situated outside but close to the surgical field (such as on a cart adjacent the operating table) such that the display 46 is directed towards the surgeon for easy visualization. The patient module 14 should be located between the patient's legs, or may be affixed to the end of the operating table at mid-leg level using a bedrail clamp. The position selected should be such that the EMG leads surgical accessories 24 can reach their farthest desired location without tension during the surgical procedure.

The information displayed to the user on the display 46 may include, but is not necessarily limited to, alpha-numeric and/or graphical information regarding any of the requested modes (e.g., Twitch Test, Free-Run EMG, Screw Test (Basic, Difference, Dynamic, Detection, and Nerve Retractor), myotome/EMG levels, stimulation levels, past stimulation events, stimulation site images, ultrasound images, etc. . . . . In one embodiment, set forth by way of example only, this information may include at least some of the following components (depending on the active mode) as set forth in Table 1:

TABLE 1

| Screen Component | Description |
|---|---|
| Spine Image | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Menu | A drop down navigation component for toggling between functions. |
| Display Area | Shows procedure-specific information including stimulation results. |
| Color Indication | Enhances stimulation results with a color display of green, yellow, or red corresponding to the relative safety level determined by the system. |
| Mode Indicator | Graphics and/or name to indicate the currently active mode (Detection, Basic Screw Test, Dynamic Screw Test, Difference Screw Test, Free-Run EMG, Twitch Test, Nerve Retractor, MEP, SSEP). In an alternate embodiment, Graphics and/or name may also be displayed to indicate the instrument in use, such as the dilator, K-wire, retractor blades, screw test instruments, and associated size information, if applicable, of the cannula, with the numeric size. If no instrument is in use, then no indicator is displayed. |

TABLE 1-continued

| Screen Component | Description |
|---|---|
| Stimulation Bar | A graphical stimulation indicator depicting the present stimulation status (i.e. on or off and stimulation current level) |
| Sequence Bar | Shows the last seven stimulation results and provides for annotation of results. |
| EMG waveforms | EMG waveforms may be optionally displayed on screen along with the stimulation results. |
| Ultrasound Image | Ultrasound images of the tissue, including bone, acquired from ultrasound transducers integrated into or used in cooperation with one or more of the surgical accessories. |

Figure 3:
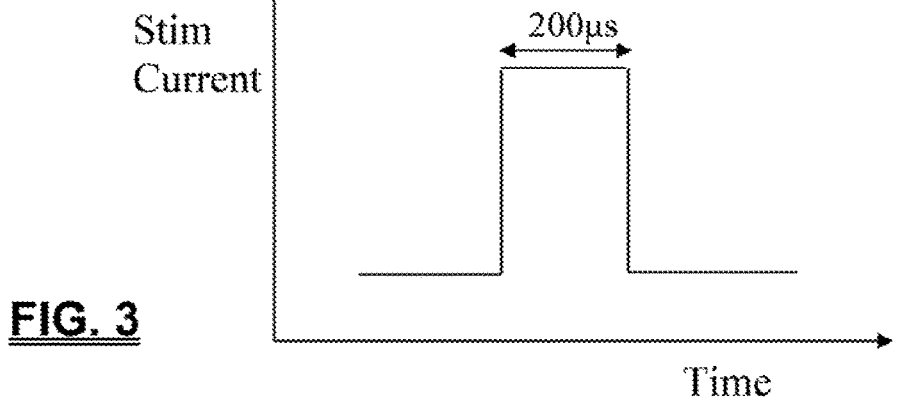
FIG. 3 is a graph illustrating an exemplary single pulse stimulation signal according to one embodiment of the present invention.
Figure 4:
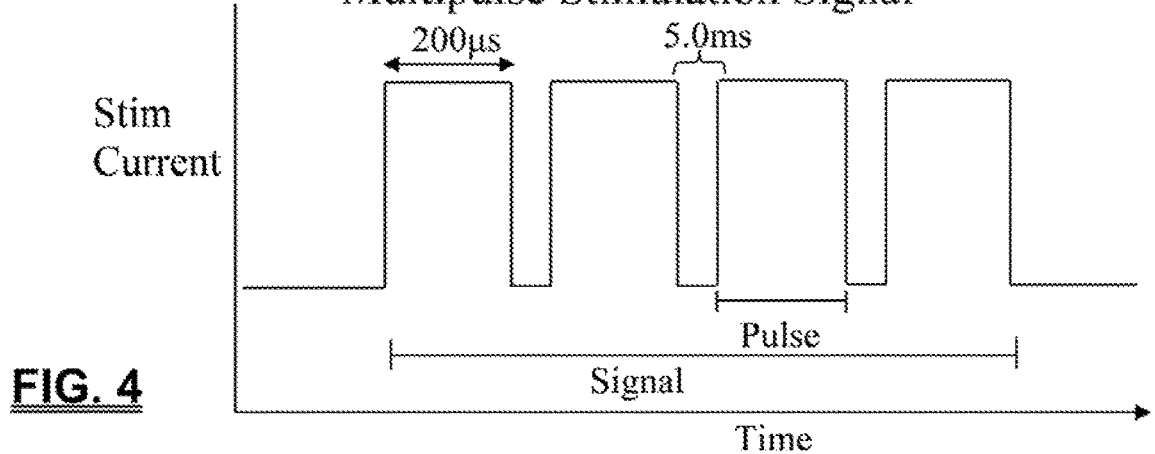
FIG. 4 is a graph illustrating an exemplary multipulse stimulation signal according to one embodiment of the present invention.
Figure 5:
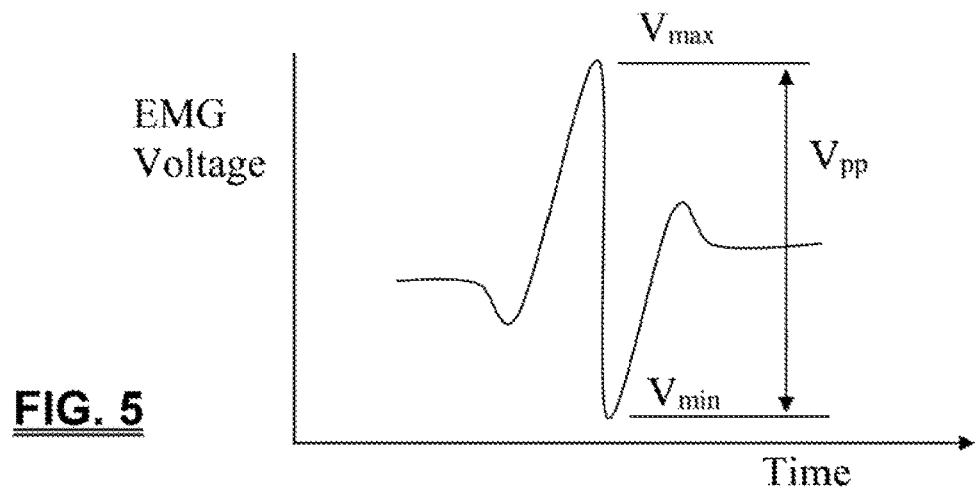
FIG. 5 is a graph illustrating an exemplary EMG response to the stimulus of FIG. 3 or 4 according to one embodiment of the present invention.

The neuromonitoring functionality of the neuromonitoring system 10 is based on assessing the evoked response of the various muscle myotomes monitored by the system 10 in relation to a stimulation signal transmitted by the system 10 (via patient module 14). This is best shown in FIG. 3-5, wherein FIG. 5 illustrates the resulting EMG of a monitored myotome in response to one of the exemplary single pulse stimulation signal shown in FIG. 3 and the multiple pulse stimulation signal shown in FIG. 4. The EMG responses provide a quantitative measure of the nerve depolarization caused by the electrical stimulus.

In one embodiment, EMG response monitoring is accomplished via 8 pairs EMG electrodes 18 (placed on the skin over the muscle groups to be monitored), a common electrode 20 providing a ground reference to pre-amplifiers in the patient module 14, and an anode electrode 22 providing a return path for the stimulation current. It should be appreciated that any of a variety of known electrodes can be employed, including but not limited to surface pad electrodes and needle electrodes. It should also be appreciated that EMG electrode placement depends on a multitude of factors, including for example, the spinal level and particular nerves at risk and user preference, among others. In one embodiment (set forth by way of example only), an exemplary EMG configuration is described for Lumbar surgery in Table 2, Thoracolumbar surgery in Table 3, and Cervical surgery in Table 4 below:

TABLE 2

Lumbar

| Color | Channel | Myotome | Nerve | Spinal Level |
|---|---|---|---|---|
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 3

Thoracolumbar

| Color | Channel | Myotome | Nerve | Spinal Level |
|---|---|---|---|---|
| Red | Right 1 | Right Abductor Pollicis Brevis | Median | C6, C7, C8, T1 |

TABLE 3-continued

Thoracolumbar

| Color | Channel | Myotome | Nerve | Spinal Level |
|---|---|---|---|---|
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 4

Cervical

| Color | Channel | Myotome | Nerve | Spinal Level |
|---|---|---|---|---|
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axillary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

Figure 6:
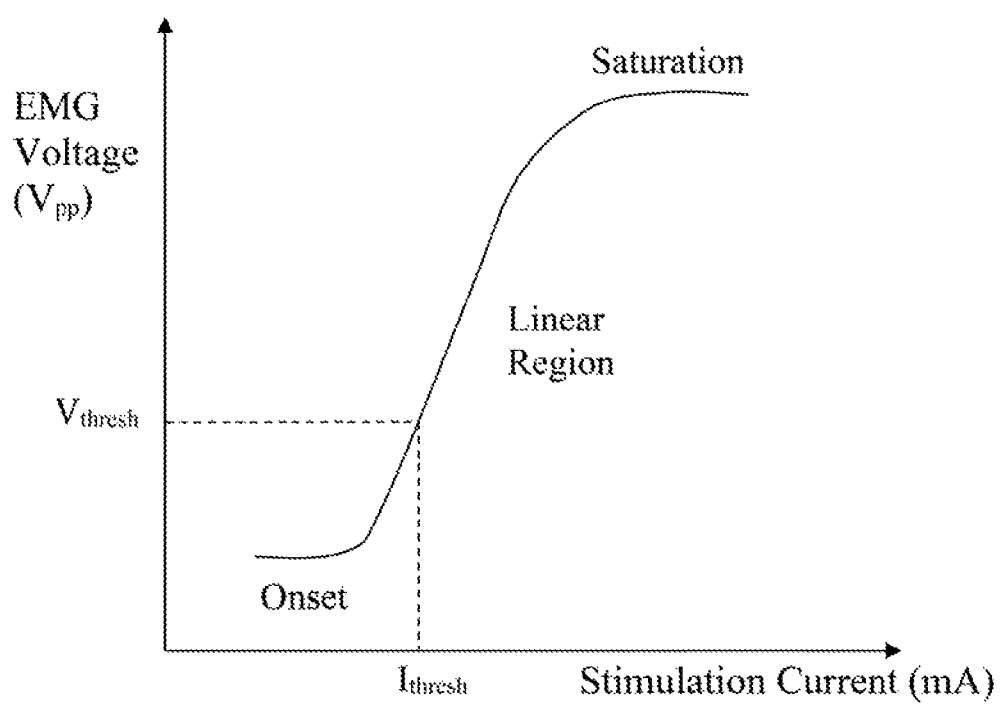
FIG. 6 is a graph illustrating a plot of peak-to-peak voltage (Vpp) for each given stimulation current level ($I_{Stim}$) forming a stimulation current pulse train according to the present invention (otherwise known as a "recruitment curve")
Figure 7A:
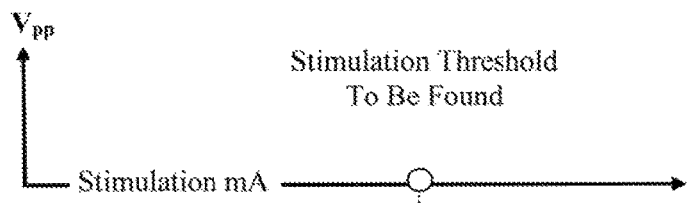
FIGS. 7A-7D are graphs illustrating the fundamental steps of a rapid current threshold-hunting algorithm according to one embodiment of the present invention.
Figure 7B:
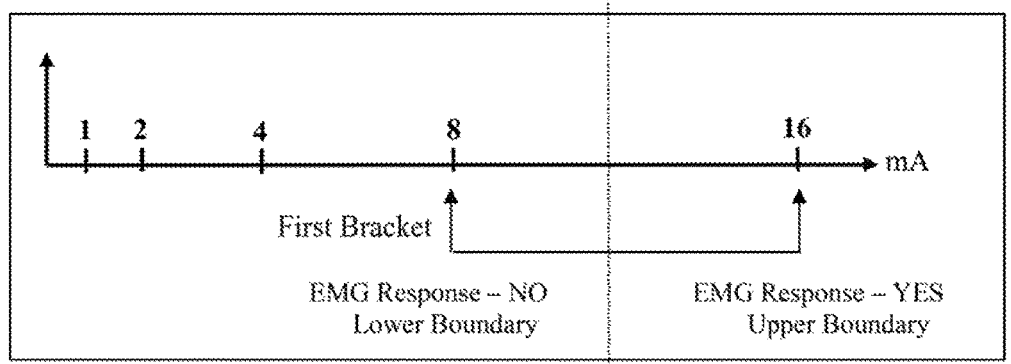
Figure 7C:
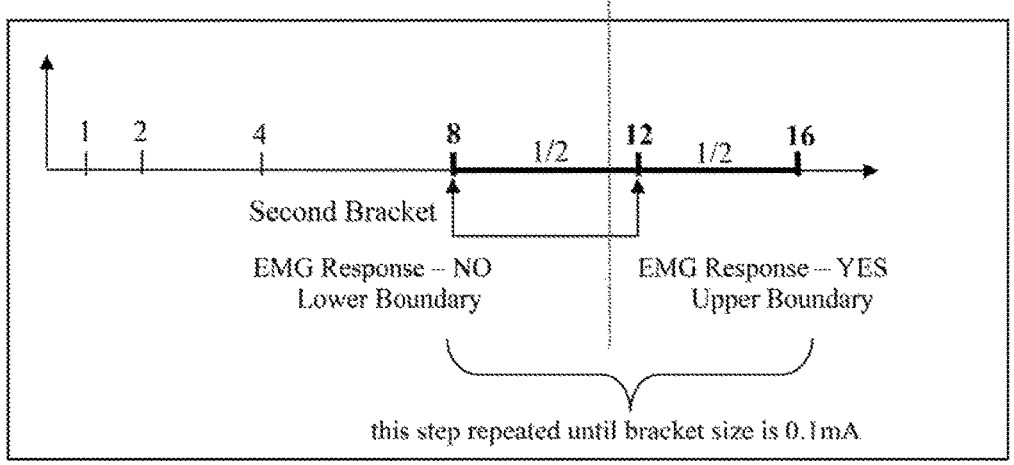
Figure 7D:
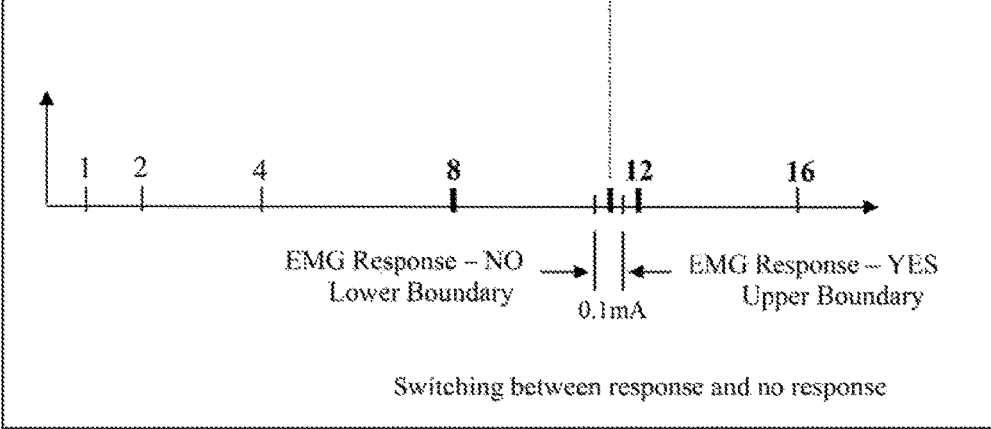
Figure 8:
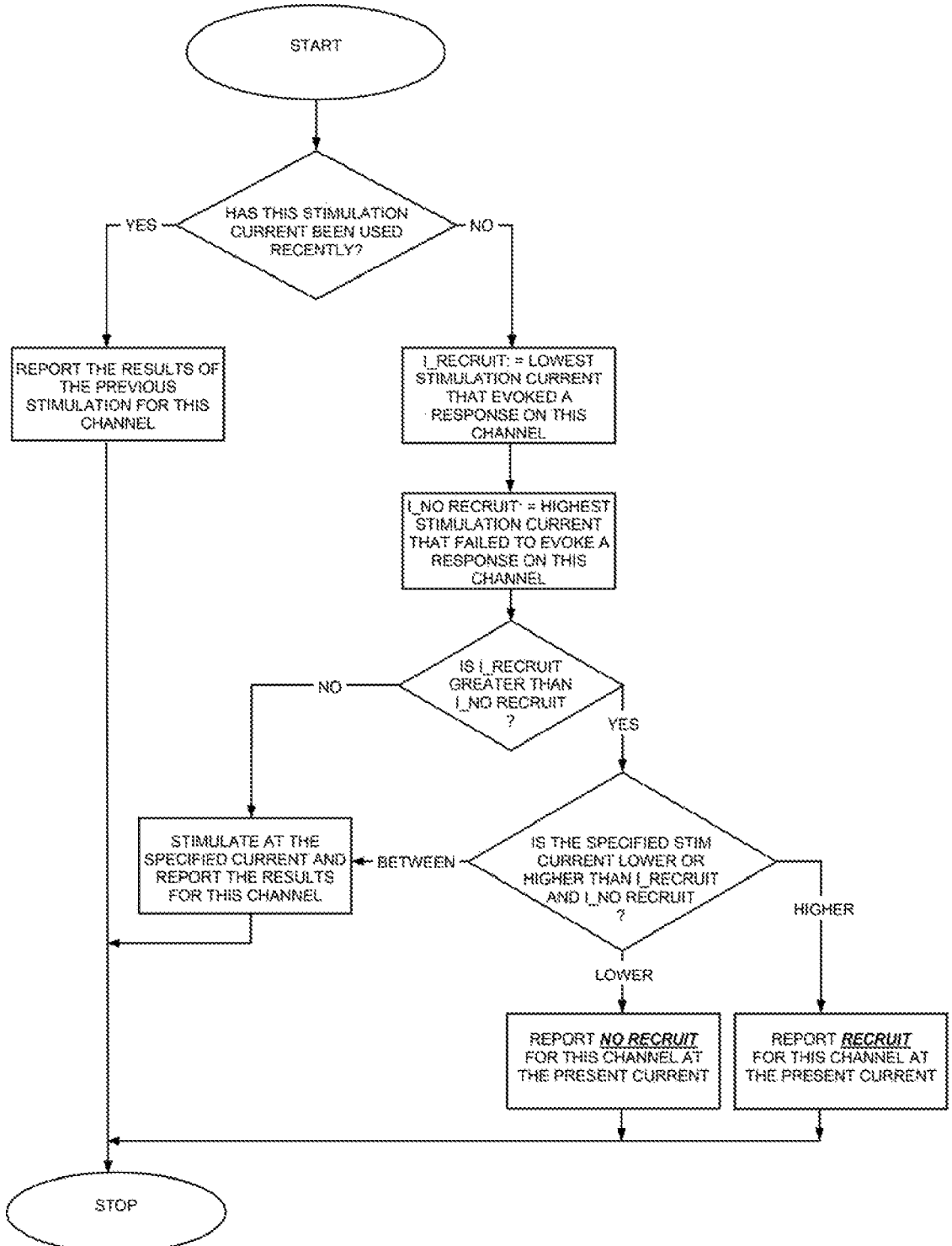
FIG. 8 is a flowchart illustrating a method by which the algorithm may omit a stimulation and proceed to the next current according to one aspect of the present invention.
Figure 9A:
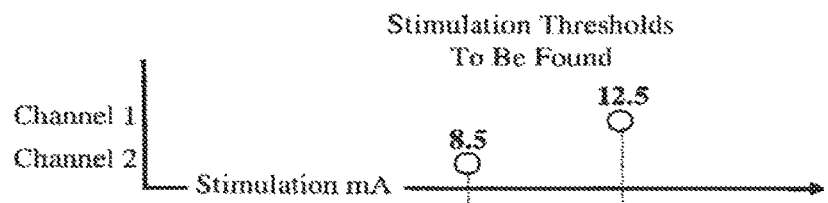
FIGS. 9A-9C are graphs illustrating use of the threshold hunting algorithm of FIG. 7 and further omitting stimulations when the likely result is already clear from previous data according to one aspect of the present invention.
Figure 9B:
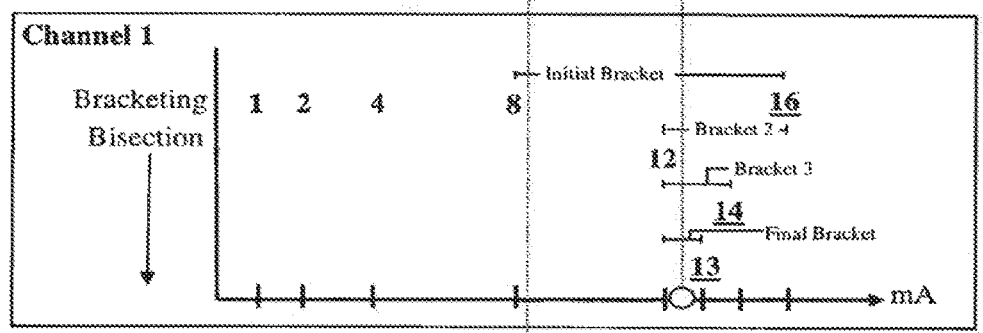
Figure 9C:
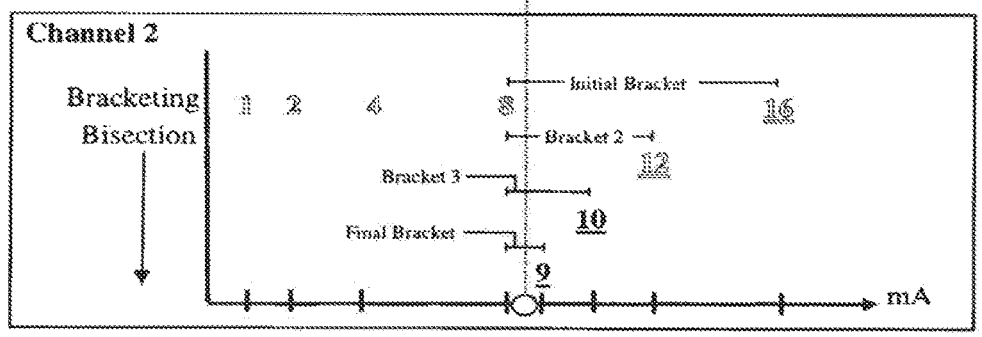
Figure 9C:
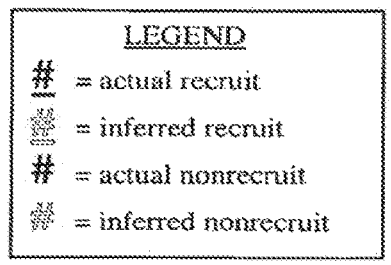

A basic premise underlying the methods employed by the system 10 for much of the neurophysiologic monitoring conducted is that neurons and nerves have characteristic threshold current levels ($I_{Thresh}$) at which they will depolarize, resulting in detectable muscle activity. Below this threshold current, stimulation signals will not evoke a significant EMG response. Each EMG response can be characterized by a peak-to-peak voltage of $V_pp=V_{max}-V_{min}$, shown in FIG. 5. Once the stimulation threshold ($I_{Thresh}$) is reached, the evoked response is reproducible and increases with increasing stimulation until saturation is reached as shown in FIG. 6. This is known as a "recruitment curve." In one embodiment, a significant EMG response is defined as having a $V_{pp}$ of approximately 100 uV. The lowest stimulation signal current, $I_{stim}$ that evokes this threshold voltage ($V_{Thresh}$) is called $I_{Thresh}$. Finding $I_{thresh}$ is useful in making neurophysiologic assessments because it provides a relative indication as to the degree of communication between a stimulation signal and nerve tissue. For example, as the degree of electrical communication between a stimulation signal and a nerve decreases, $I_{thresh}$ will increase. Conversely, as the degree of communication between the stimulation signal and a nerve increases, $I_{thresh}$ will decrease.

The neuromonitoring system 10 capitalizes on and enhances the information derived from $I_{thresh}$ by (a) employing methods designed to find $I_{thresh}$ quickly, accurately, and efficiently; (b) analyzing $I_{thresh}$ according to predetermined safety indicator levels; and (c) displaying $I_{thresh}$ and related safety indication data in a simple and meaningful way. Armed with the useful information conveyed by the system 10, the surgeon may detect early on any problem or potential problem and then act to avoid and/or mitigate the situation. By way of general example only, an excessively high $I_{thresh}$ or an increase over a previous $I_{thresh}$ measurement during Nerve Retractor mode may indicate a deterioration of nerve root function caused by excessive and/or prolonged retraction. During Screw Test and Detection modes, a low $I_{thresh}$ value may indicate a breach in the pedicle, or the close proximity of a nerve, respectively.

To quickly determine $I_{thresh}$, the system 10 may employ a variety of suitable algorithms and techniques which are described in detail in the "NeuroVision Applications," all of which are incorporated by reference below, as if they were set forth herein in their entireties. One exemplary threshold hunting algorithm, illustrated by way of example only in FIGS. 7A-7D, is described hereafter in only brief detail. The threshold hunting algorithm utilizes a bracketing method and a bisection method to find $I_{thresh}$. The bracketing method finds a range (bracket) of stimulation currents that must contain $I_{thresh}$. To accomplish this, the algorithm directs stimulation to begin at a predetermined current level (based on the selected function). For each subsequent stimulation, the current level is doubled from the previous current level. This doubling continues until a until a stimulation current recruits, that is, results in an EMG response with a $V_{pp}$ greater or equal to $V_{thresh}$ (e.g. 100 uV). This first stimulation current to recruit, together with the last stimulation current to have not recruited, forms the initial bracket. If the stimulation current threshold, $I_{thresh}$, of a channel exceeds a maximum stimulation current, that threshold is considered out of range.

After the bracket containing the threshold current $I_{thresh}$ has been determined, the initial bracket is successively reduced via the bisection method to a predetermined width. This is accomplished by applying a first bisection stimulation current that bisects (i.e. forms the midpoint of) the initial bracket. If this first bisection stimulation current recruits, the bracket is reduced to the lower half of the initial bracket. If this first bisection stimulation current does not recruit, the bracket is reduced to the upper half of the initial bracket. This process is continued for each successive bracket until $I_{thresh}$ is bracketed by stimulation currents separated by the predetermined width. In one embodiment, the midpoint of this final bracket may be defined as $I_{thresh}$; however, any value falling within the final bracket may be selected as $I_{thresh}$ without departing from the scope of the present invention.

During some functions (e.g. Screw Tests and Detection) stimulations may stop after $I_{thresh}$ is determined for the channel possessing the lowest $I_{thresh}$. For other functions (e.g. Nerve Retractor), however, it may useful to determine $I_{thresh}$ for every channel. To accomplish this quickly, the hunting algorithm may employ additional methods allowing it to omit certain stimulations, thereby reducing the number of stimulations and time required to obtain an $I_{thresh}$ value on each channel. As demonstrated in FIG. 8 and FIGS. 9A-9C, $I_{thresh}$ is still found using the bracketing and bisection methods described above, however the algorithm will omit stimulations for which the result is predictable from data previously acquired. When a stimulation signal is omitted, the algorithm proceeds as if the stimulation had taken place. This permits the algorithm to proceed to the next required stimulation immediately, without a time delay inherently associated with each stimulation signal. To further reduce the number of stimulations required over the time frame of an entire surgical procedure, the algorithm may confirm previously obtained $I_{thresh}$ values (e.g. by stimulation at current levels just below and at/or just above $I_{thresh}$ and determining whether the resulting responses are consistent with the previously acquired $I_{thresh}$ value), rather than initiating stimulations from the beginning each time a function is performed.

By way of example only, the various functional modes of the neuromonitoring system 10 may include the Basic Screw Test, Difference Screw Test, Dynamic Screw Test, MaXcess® Detection, and Free-run EMG, all of which will be described briefly below. The Basic Screw Test, Difference Screw Test, and Dynamic Screw Test modes are designed to assess the integrity of bone (e.g. pedicle) during all aspects of pilot hole formation (e.g., via an awl), pilot hole preparation (e.g. via a tap), and screw introduction (during and after). These modes are described in greater detail in commonly owned U.S. Pat. No. 7,664,544 entitled "System and Methods for Performing Percutaneous Pedicle Integrity Assessments" and commonly owned U.S. Pat. No. 7,657,308, entitled "System and Methods for Performing Dynamic Pedicle Integrity Assessments," the entire contents of which are both hereby incorporated by reference as if set forth fully herein. The MaXcess® Detection mode is designed to detect the presence of nerves during the use of the various surgical access instruments of the neuromonitoring system 10, including the k-wire 62, dilator 64, cannula 66, 68, retractor assembly 70. This mode is described in greater detail within commonly owned U.S. Pat. No. 8,068,912 entitled "System and Methods for Determining Nerve Proximity, Direction, and Pathology During Surgery," the entire contents of which is hereby incorporated by reference as if set forth fully herein. Although not described herein, various other functional modes may be performed by the system 10, such as for example only, MEP and SSEP functions which are described in detail within commonly owned and co-pending Int'l Patent App. No. PCT/US2006/003966, entitled "System and Methods for Performing Neurophysiologic Assessments During Spine Surgery," filed on Feb. 2, 2006, the entire contents of which are hereby incorporated by reference as if set forth fully herein; The Twitch Test mode which is described in detail in commonly owned U.S. Pat. No. 8,538,539 entitled "System and Methods for Assessing the Neuromuscular Pathway Prior to Nerve Testing," the entire contents of which is hereby incorporated by reference as if set forth fully herein; and Nerve Retractor mode which is described in greater detail within commonly owned U.S. Pat. No. 7,522,953 entitled "System and Methods for Performing Surgical Procedures and Assessments," the entire contents of which are hereby incorporated by reference as if set forth fully herein.

Figure 10:
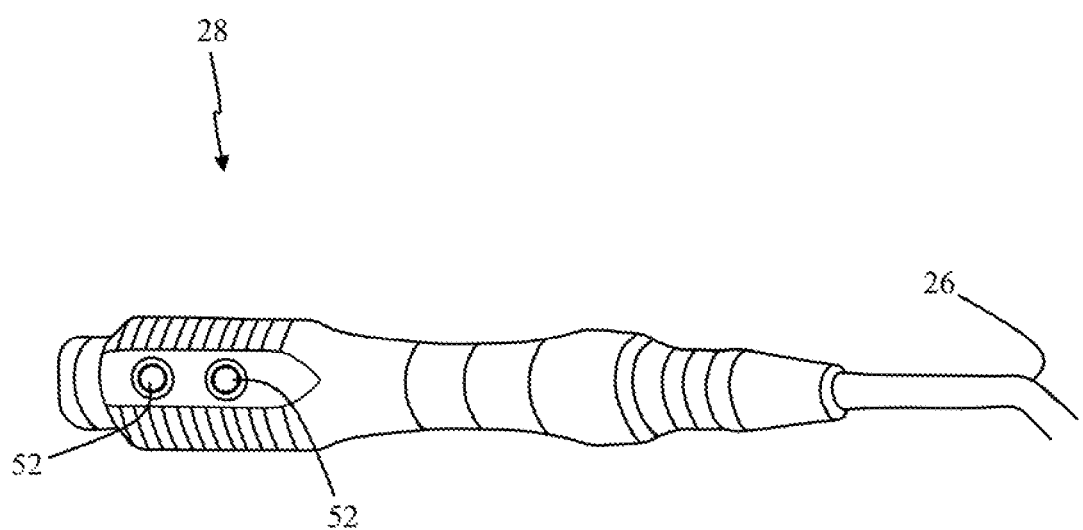
FIG. 10 is an illustration of a stimulation handpiece for coupling surgical accessories to the neuromonitoring system 10 according to one embodiment of the present invention.

In one embodiment one or more of the surgical accessories 24 including, but not necessarily limited to screw test probe 30, tap member 32, bone awl 34, k-wire 36, dilating cannulae 38, 40, retractor assembly 42, by way of fixed or releasable linkage to a stimulation handpiece 28. Turning to FIG. 10, there is shown one exemplary embodiment of a stimulation handpiece 28. Stimulation handpiece 28 is communicatively linked to the patient module 14 via accessory cable 26. Stimulation handpiece 28 directs stimulation signals from the patient module 14 to the surgical accessories 24. Thereafter the stimulation signal preferably exits one or more electrode regions formed at or near the distal ends of the surgical accessories 24. Stimulation handpiece 28 may be equipped with one or more stimulation buttons 52 for selectively applying electrical stimulation to the attached surgical accessory 24 (according to the selected mode and hunting algorithm discussed above). The one or more stimulation buttons 52 are preferably positioned along stimulation handpiece 28 such that the one or more buttons 52 may preferably be manipulated using the thumb and/or one or more fingers of the hand in which handpiece 28 is held. Various surgical accessories 24 that may be coupled to the stimulation handpiece 28 will be discussed in more detail with regard to the neurophysiologic assessment modes performed by the neuromonitoring system 10.

Figure 11:
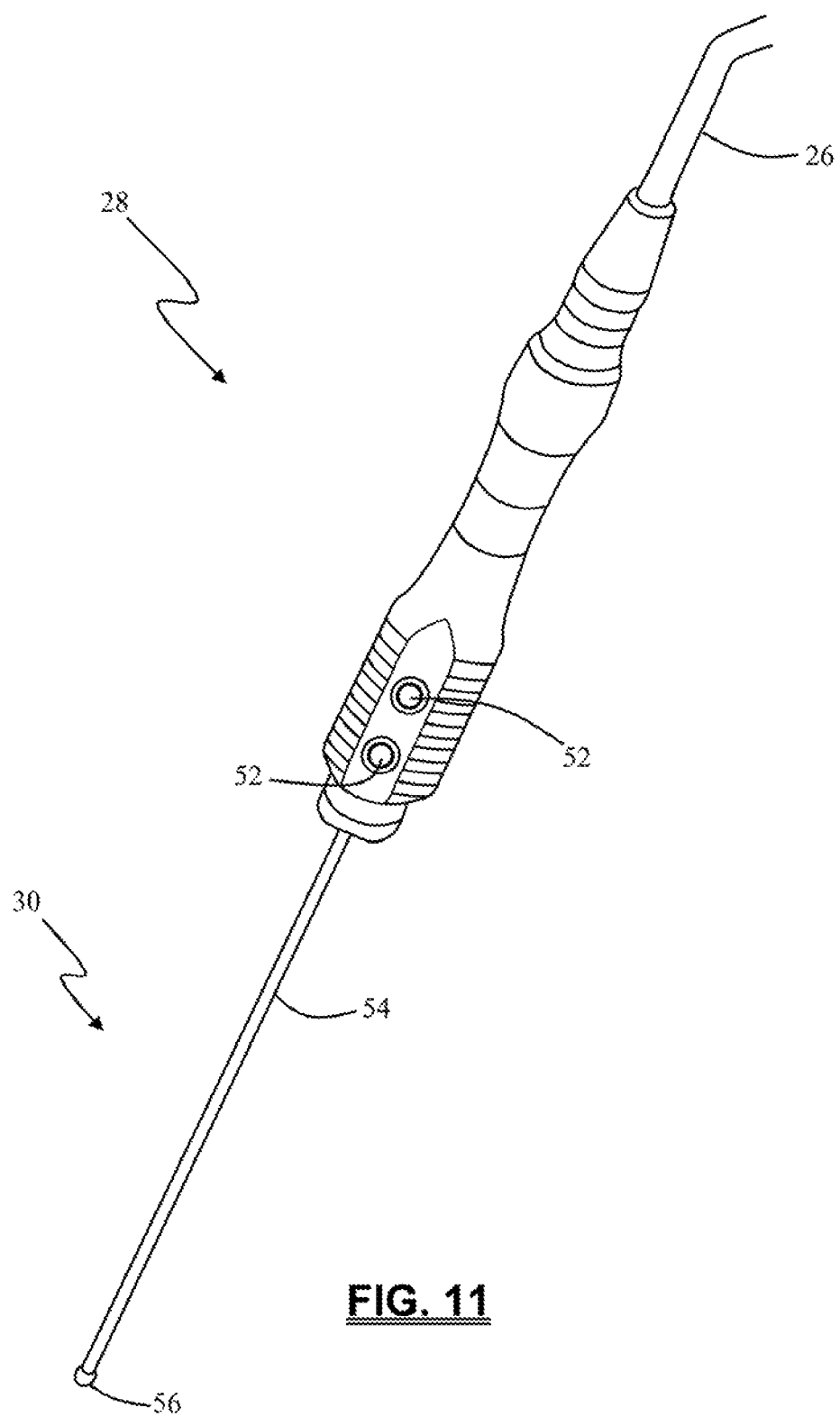
FIG. 11 an of a screw test probe coupled to the stimulation handpiece of FIG. 10 illustration according to one embodiment of the present invention.

The neuromonitoring system 10 may test the integrity of pedicle holes (during and/or after formation) and/or screws (during and/or after introduction) via the Basic Screw test, Difference Screw Test, and/or Dynamic Screw Test modes. For the Basic Screw Test a screw test probe 30, such as that illustrated in FIG. 11, is used to direct stimulation signals to a pilot hole prior to screw installation, or a screw head after screw installation. Screw test probe 30 may be coupled to stimulation handpiece 28 and includes an elongated probe member 54 and a ball-tipped end 56. The ball-tipped end 56 is inserted through the surgical corridor to the stimulation target site (e.g. pilot hole and or screw head). Once the ball-tipped end 56 is in position, a stimulation button 52 may be pressed to initiate stimulation. The insulating character of bone will prevent the stimulation current, up to a certain amplitude, from communicating with the nerve, thus resulting in a relatively high $I_{thresh}$, as determined via the threshold hunting algorithm described above. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. Details and results of the Basic Screw test results and may be conveyed to the user on display 46.

In Difference Screw Test mode, a baseline threshold value is determined by directly stimulating a nerve. Screw test probe 30 may preferably be used, and the probe is advanced through the surgical corridor to the surgical target site (i.e. the nerve to be directly stimulated). Button 52 on the stimulation handpiece 28 is pressed to initiate stimulation and a baseline threshold is established. Screw test probe 30 may then be maneuvered to the next stimulation target site (e.g. pilot hole or screw head) and stimulation is initiated to determine the actual threshold value $I_{thresh}$. The actual threshold is compared to the baseline threshold. The difference between the actual and baseline thresholds is calculated to provide an indication of the safety level. Details and results, including the baseline, actual, and difference thresholds among other things may be displayed for the user on GUI display 46.

Figure 12:
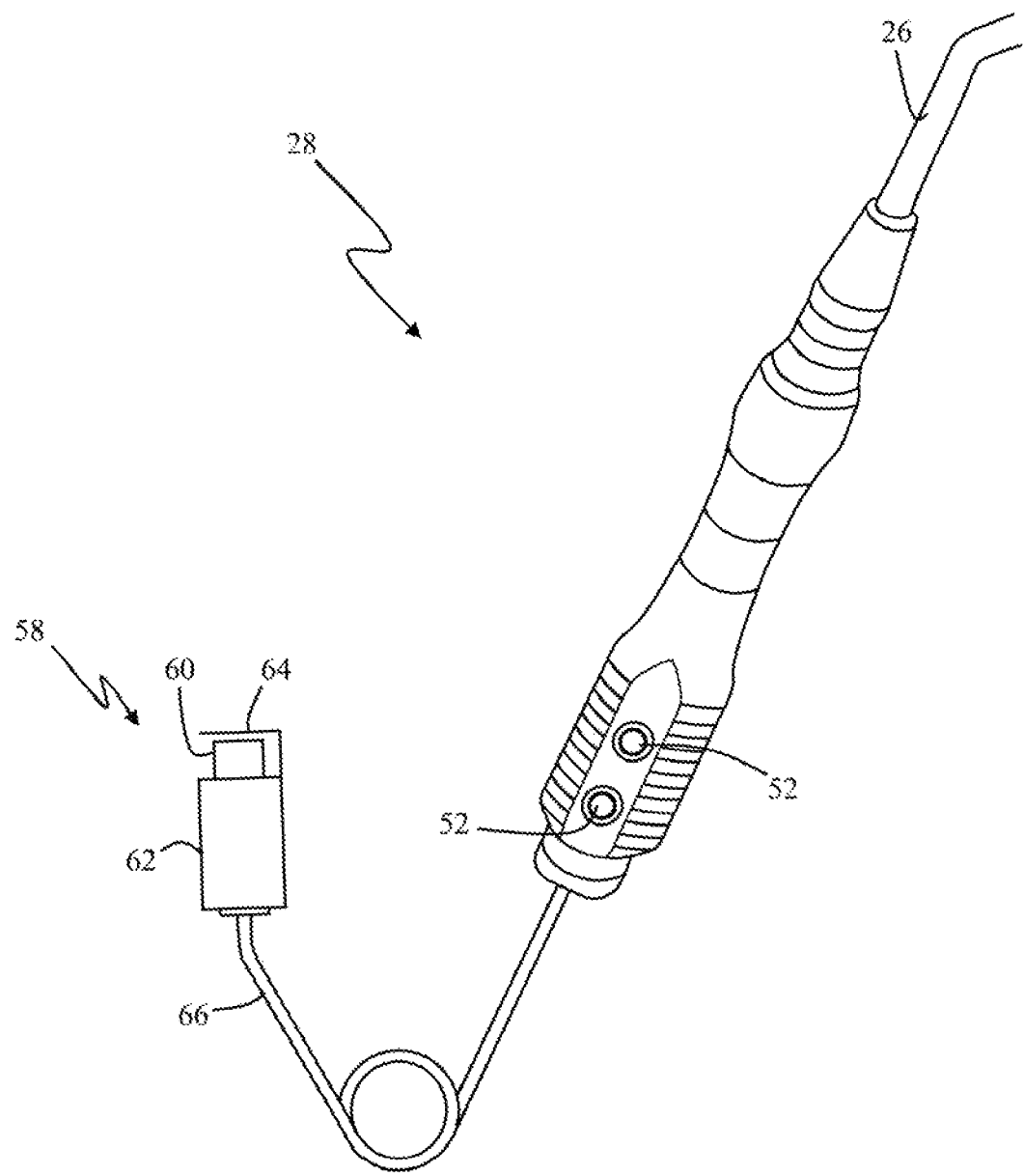
FIG. 12 is an illustration of a stimulation clip coupled to the stimulation handpiece of FIG. 10 according to one embodiment of the present invention.

Dynamic Screw Test mode continuously monitors threshold values while one or more surgical accessories are in use, for example forming a pilot hole. For dynamic screw tests an electric coupling device, such as, by way of example only, stimulation clip 58 is coupled to stimulation handpiece 28, as illustrated in FIG. 12. The electric coupling device couples surgical accessories 24 (such as for example, a tap member 32 or a bone awl 34) to the neuromonitoring system 10 such that stimulation signals may be transmitted through the tool during use. Thus, screw testing may be performed continuously during pilot hole formation by coupling the bone awl 34 to the neuromonitoring system 10, and during pilot hole preparation by coupling the tap 32 to the system 10. Likewise, by coupling a pedicle screw to the neuromonitoring system 10 (such as via pedicle screw instrumentation), screw testing may be performed during screw introduction. To continually update the $I_{thresh}$ results in an efficient manner, the algorithm may preferably confirm the earlier results by switching back and forth between stimulation signals just above and just below $I_{thresh}$. If the expected results are not obtained then the algorithm may transition back into the bracketing and bisection steps. Details and results of the Dynamic Screw test results and may be conveyed and continuously updated on display 46.

Figure 13:
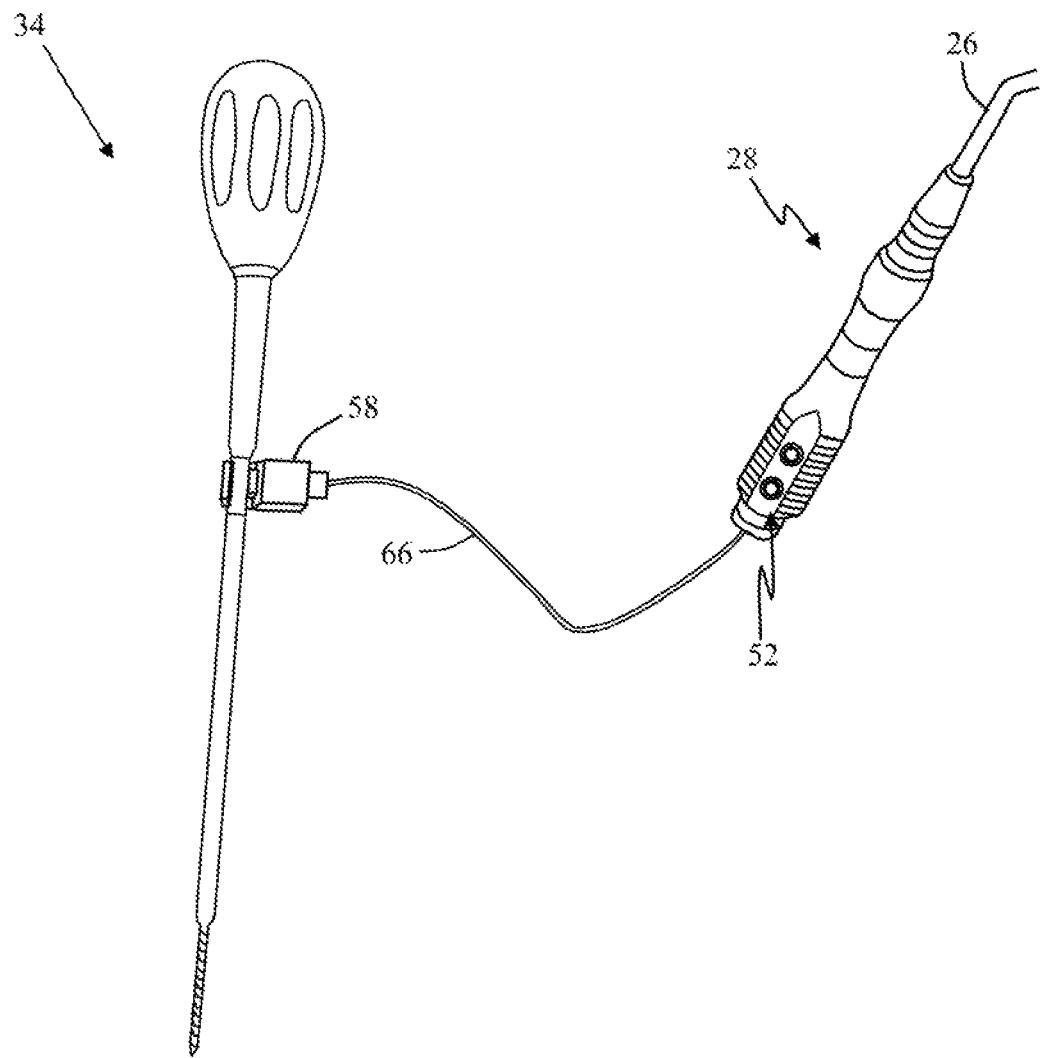
FIG. 13 is a side view of the stimulation probe of FIG. 11 positioned over a stimulation target site and wherein the distal tip of the probe member and the stimulation target site are included in the camera's field of view.

With reference to FIG. 1 and FIG. 12, stimulation clip 58 utilizes a spring-loaded plunger to hold the surgical tool and transmit the stimulation signal. The plunger 60 is composed of a conductive material such as metal. A nonconductive housing 62 partially encases the plunger 60 about its center. Extending from the housing 62 is an end plate 64. An electrical cable 66 connects the stimulation clip 58 to the stimulation handpiece 28. A spring (not shown) is disposed within the housing 62 such that in a natural or "closed" state the plunger 60 is situated in close proximity to the endplate 64. Exerting a compressive force on the spring (such as by pulling the cable 66 while holding the housing 62) causes a gap between the end plate 64 and the plunger 60 to widen to an "open" position, thereby allowing insertion of a surgical tool (e.g. tap member 32 and awl 34) between the end plate 64 and plunger 60. Releasing the cable 66 allows the spring to return to a "closed" position, causing the plunger 60 to move laterally back towards the endplate such that a force is exerted upon the surgical instrument and thereby holds it in place between the endplate 64 and the plunger 60. This is best viewed in FIG. 13 wherein stimulation clip 58 is linked to stimulation handpiece 28 (via cable 66) on one end and coupled around tap member 32 on the other end. Alternatively, stimulation clip 58 (or clap 68 described below) may be linked directly to patient module 14 rather than stimulation handpiece 28, in which case stimulation may be initiated and/or stopped from the GUI display 46. The electrical stimulus may be initiated by pressing one of stimulation buttons 52 and thereafter the stimulation signal may be passed from the handpiece 28 through the cable 66 and plunger 60 to the tap member 32 (or other surgical accessory 24).

Again with reference to FIG. 1, there is shown another embodiment of an electric coupling device for use with the system 10. Stimulation clamp 68 is comprised of two prongs hingedly coupled at a coupling point 70 such that the clamp 68 includes an attachment end 72 and a non-attachment end 74. A stimulation electrode 76 is disposed on the attachment end 72 and communicates with electric cable 66 extending from the non-attachment end 74 to the handpiece 28. In a "closed" position the prong ends at the attachment end 72 touch. Depressing the prongs at the non-attachment end 74 in a direction towards one another causes a gap to form between the prong ends at the attachment end 72. Positioning the "opened" attachment end 72 over a desired surgical instrument and releasing the force on the non-attachment end 74 causes the attachment end 72 to pinch tight on the surgical accessory 24 and thereby allow the electrical stimulus to pass from the stimulation handpiece 28, through the stimulation electrode 76, to the surgical accessory.

Figure 14:
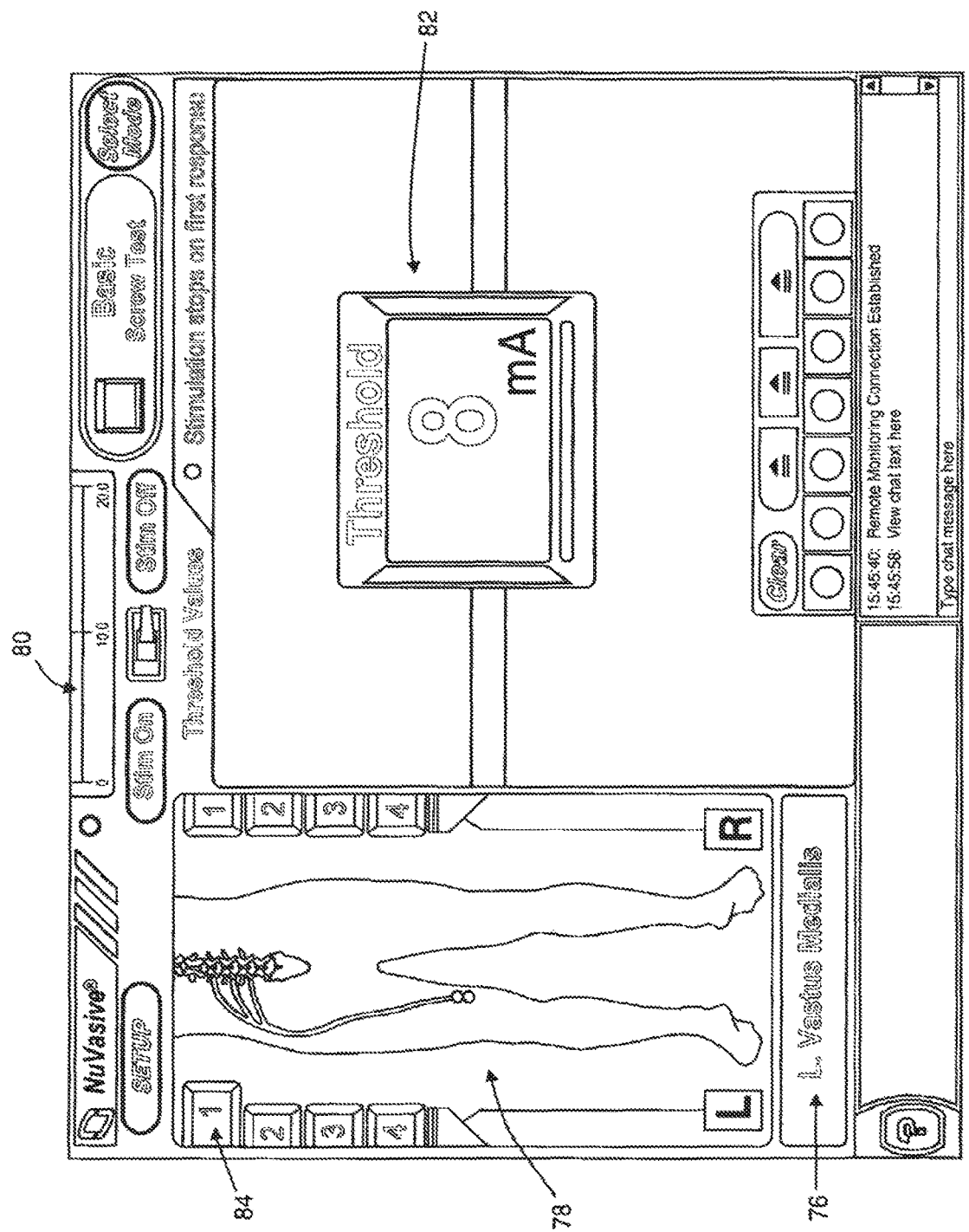
FIG. 14 is an exemplary screen view of the Basic Screw Test mode for performing pedicle integrity assessments according to one embodiment of the present invention.
Figure 15:
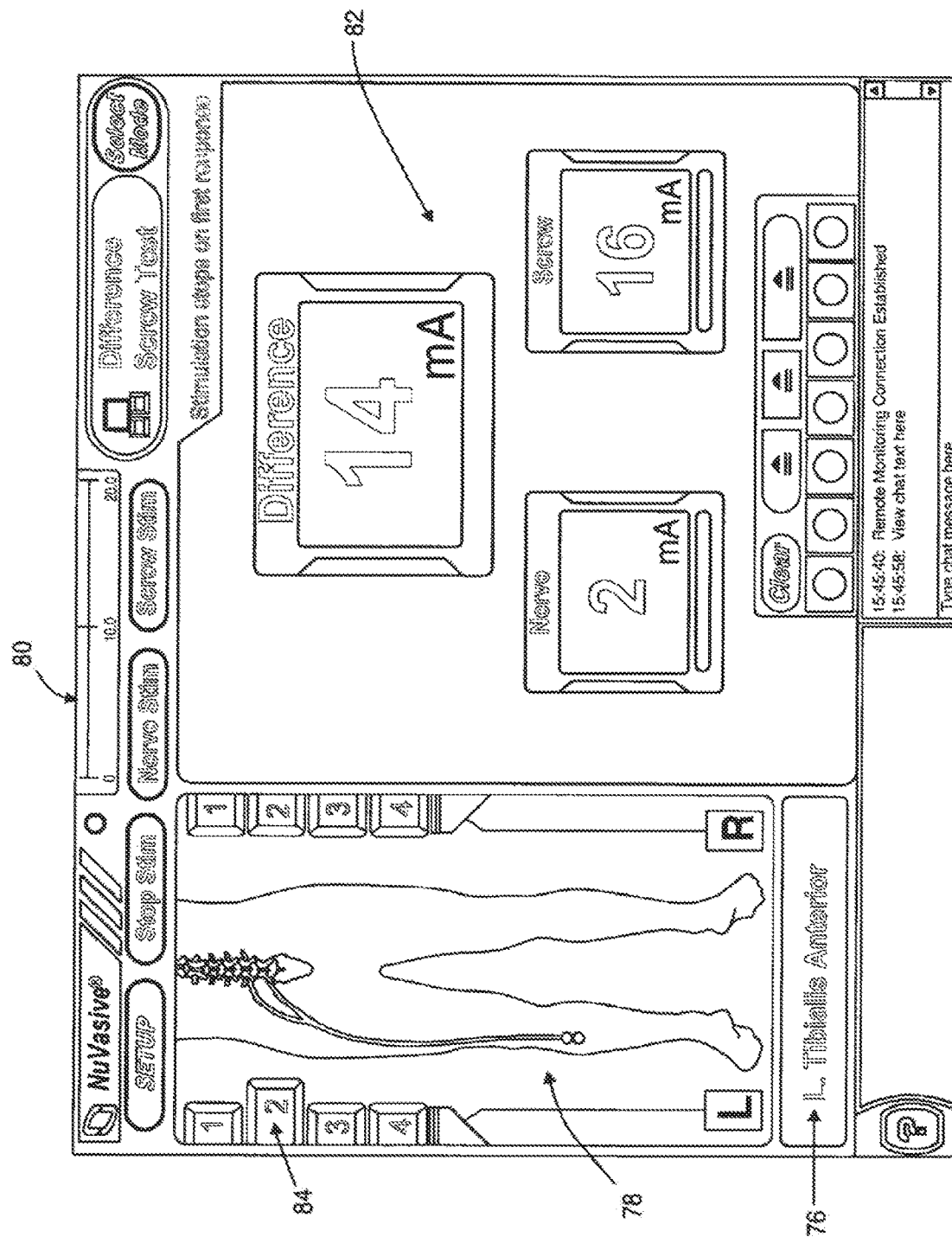
FIG. 15 is an exemplary screen view of the Difference Screw Test mode for performing pedicle integrity assessments according to one embodiment of the present invention.
Figure 16:
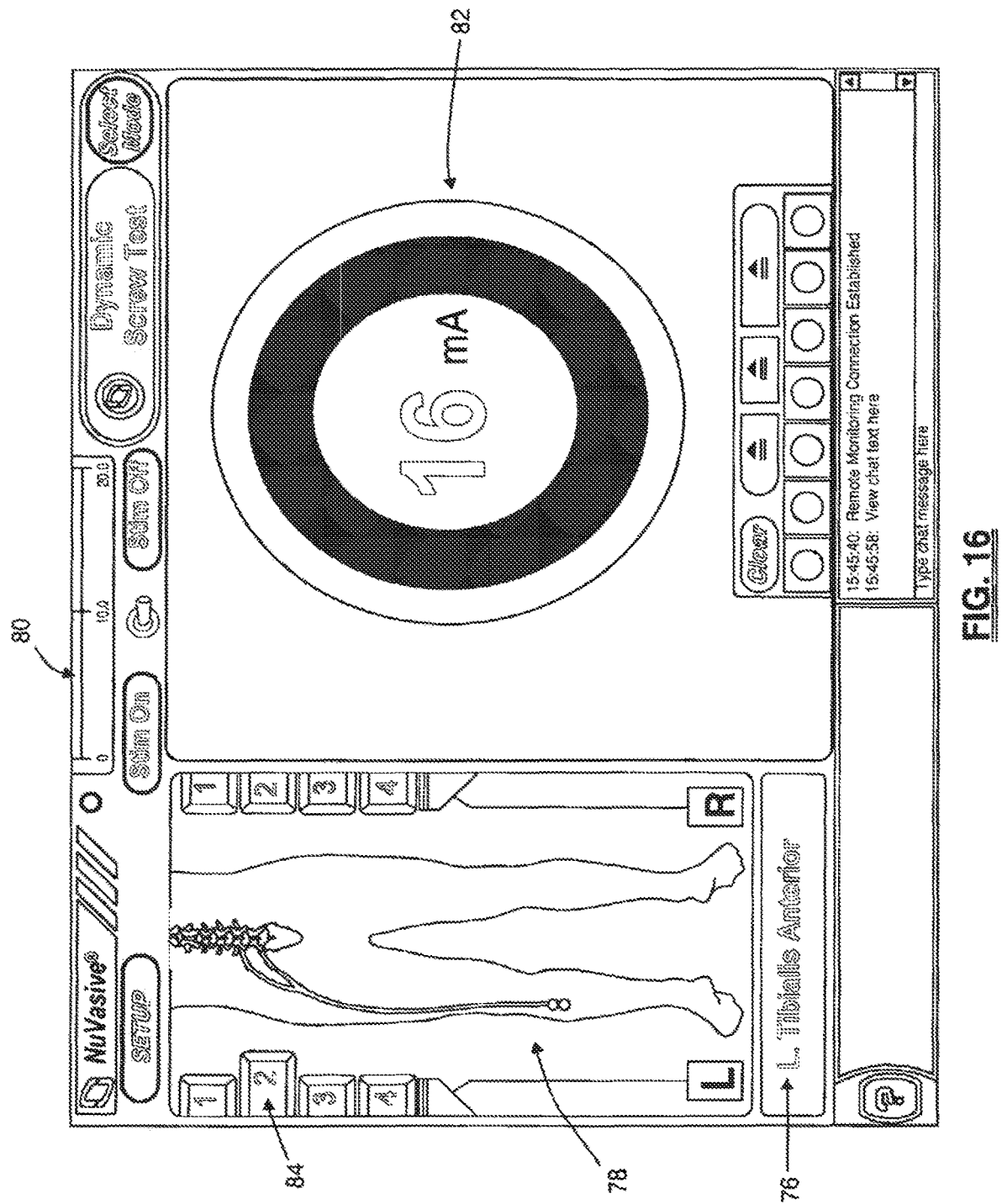
FIG. 16 is an exemplary screen view of the Dynamic Screw Test mode for performing pedicle integrity assessments according to one embodiment of the present invention.

Stimulation results and other relevant data for the screw test modes are conveyed to the user on display 46, as illustrated in FIGS. 14-16. FIG. 14 is an exemplary screen view of the Basic Screw Test mode for display on display 46. FIG. 15 illustrates an exemplary screen view of the Difference Screw Test mode for display on display 46. FIG. 16 is an exemplary screen view of the Dynamic Screw Test mode for display on display 46. Upon execution of the algorithm, one or more channel tabs may be highlighted using a color-code to indicate status of the corresponding nerve, and thus the relative safety level determined by the system 10. The channel with the "worst" (lowest) level will preferably be enlarged and that myotome name 76 will be displayed, as well as graphically depicted on the spine diagram 78. A vertical bar chart 80 may also be shown to depict the stimulation current required to evoke a significant response for the selected channel. A large numerical readout 82 may also indicate the value of the stimulation result. Preferably, the display of the stimulation result may be augmented with a color code utilizing the colors green, yellow, and red to enhance the understandability of the result and quickly indicate to the surgeon the level of safety determined by the system 10. Red may be used to indicate an $I_{thresh}$ level below a predetermined unsafe level. Yellow may be used to indicate an $I_{thresh}$ that falls in between predetermined safe and unsafe levels. Green may represent an $I_{thresh}$ within the range predetermined as safe. Although not show, the threshold results may be replaced with, or more preferably, augmented with a display of the actual waveform for each channel, as well as audible sounds distinctive to each level of safety (safe, unsafe, in between).

The neuromonitoring system 10 may perform nerve proximity testing, via the MaXcess® Detection mode, to ensure safe and reproducible access to surgical target sites. Using the surgical access components 36-40, the system 10 detects the existence of neural structures before, during, and after the establishment of an operative corridor through (or near) any of a variety of tissues having such neural structures, which, if contacted or impinged, may otherwise result in neural impairment for the patient. The surgical access components 36-40 are designed to bluntly dissect the tissue between the patient's skin and the surgical target site. Access components 36-40 preferably utilize stimulation handpiece 28 and stimulation clip 58 (in the same manner as described above and shown in FIG. 12) to link to the system 10. Cannulae or dilators of increasing diameter may be advanced towards the target site until a sufficient operating corridor is established. As the cannulae or dilators are advanced to the target site, electrical stimulation signals are transmitted through the stimulation handpiece 28 to the distal end of the cannulae where they are emitted from an electrode region. The stimulation signal will stimulate nerves in close proximity to the stimulation electrode and the corresponding EMG response is monitored. As a nerve gets closer to the stimulation electrode, the stimulation current ($I_{stim}$) required to evoke a muscle response decreases. $I_{thresh}$ is calculated (using the threshold hunting algorithm described above) which provides a measure of the communication between the stimulation signal and the nerve and thus giving a relative indication of the proximity between access components and nerves.

Additional and/or alternative surgical access components such as, by way of example only, a tissue retraction assembly 42 (FIG. 1) may be coupled to the system 10 (via stimulation clip 58 or clamp 68) and employed to provide safe and reproducible access to a surgical target site. Tissue retraction assembly 42 and various embodiments and uses thereof have been shown and described co-pending and commonly assigned U.S. patent application Ser. No. 10/967, 668, entitled "Surgical Access System and Related Methods," filed on Oct. 18, 2004, the entire contents of which are expressly incorporated by reference as if set forth herein in their entirety.

Figure 17:
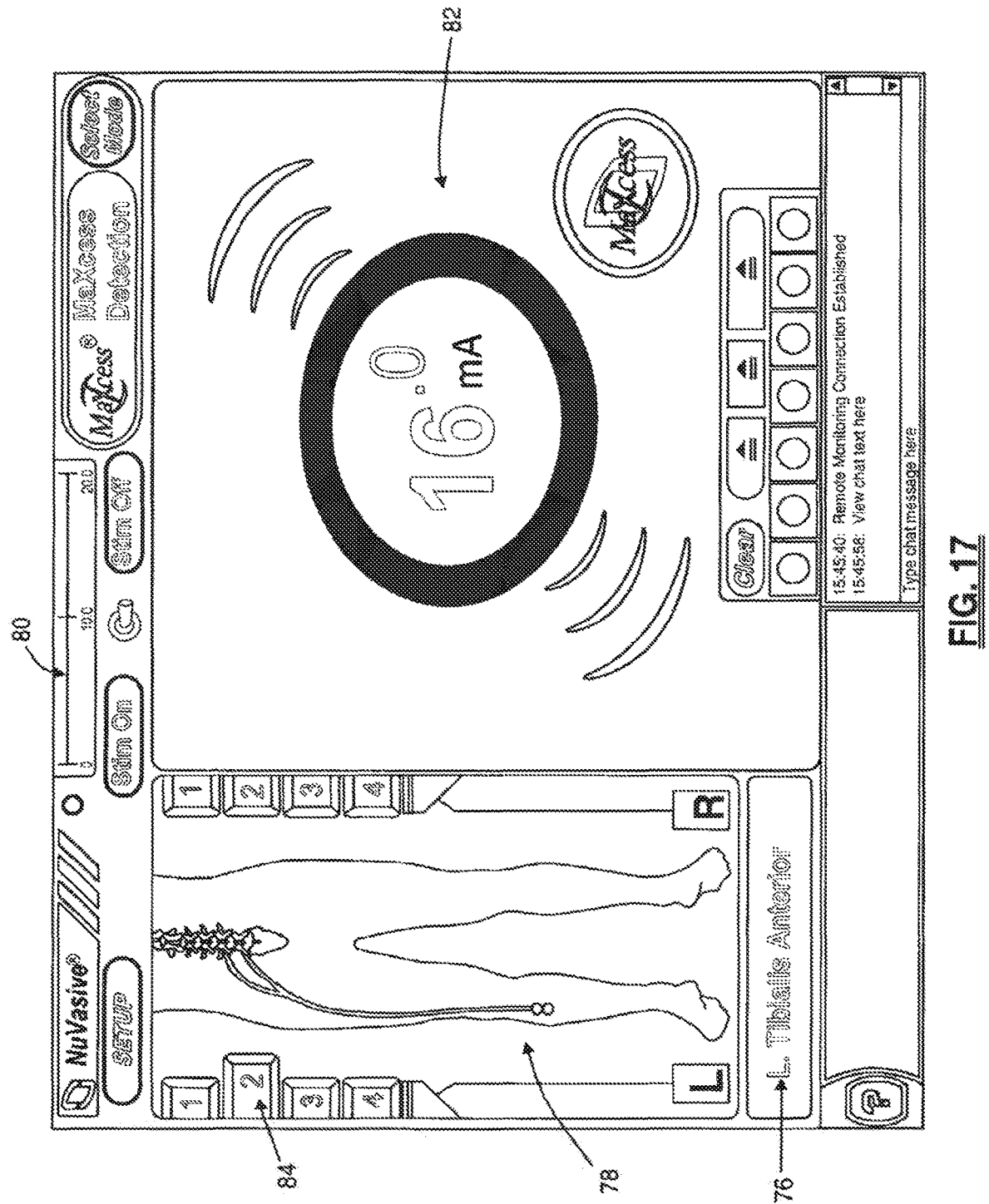
FIG. 17 is an exemplary screen view of the MaXcess Detection mode for detecting nerve presence during spinal access according to one embodiment of the present invention.

An exemplary screen display of the Detection mode for display on display 46 is illustrated by way of example only in FIG. 17. Similar to the screw test modes, upon execution of the algorithm, one or more channel tabs may be highlighted using a color-code to indicate status of the corresponding nerve, and thus the relative safety level determined by the system 10. The channel with the "worst" (lowest) level will preferably be enlarged and that myotome name 76 will be displayed, as well as graphically depicted on the spine diagram 78. A vertical bar chart 80 may also be shown to depict the stimulation current required to evoke a significant response for the selected channel. A large numerical readout 82 may also indicate the value of the stimulation result. Preferably, the display of the stimulation result may be augmented with a color code utilizing the colors green, yellow, and red to enhance the understandability of the result and quickly indicate to the surgeon the level of safety determined by the system 10. Red may be used to indicate an $I_{thresh}$ level below a predetermined unsafe level. Yellow may be used to indicate an $I_{thresh}$ that falls in between predetermined safe and unsafe levels. Green may represent an $I_{thresh}$ within the range predetermined as safe. Although not show, the threshold results may be replaced with, or more preferably, augmented with a display of the actual waveform for each channel, as well as audible sounds distinctive to each level of safety (safe, unsafe, in between).

The neuromonitoring system 10 may also conduct free-run EMG monitoring while the system is in any of the above-described modes. Free-run EMG monitoring continuously listens for spontaneous muscle activity that may be indicative of potential danger. The system 10 may automatically cycle into free-run monitoring after 5 seconds (by way of example only) of inactivity. Initiating a stimulation signal in the selected mode will interrupt the free-run monitoring until the system 10 has again been inactive for five seconds at which time the free-run begins again. Stimulated and/or Free-run results for any function may be replaced with, or more preferably, augmented with a display of the actual waveform for each channel, as well as audible sounds distinctive to each level of safety (safe, unsafe, in between).

To augment the neurophysiologic assessments, such as for example only those described above, performed by the neuromonitoring system 10, the system 10 may be further equipped to conduct and display ultrasound imaging of proximate body tissues (e.g. bone during pilot hole formation and preparation and/or screw implantation and nerves and/or vasculature during surgical access). To do so, the system 10 may employ intraoperative ultrasound tailored to allow use within bone, such as, by way of example only, the ultrasound system described in U.S. Pat. No. 6,579,244, entitled "Intraosteal Ultrasound During Surgical Implantation." Specifically, at least one ultrasound transducer 55 may be deployed to the surgical target site during surgery. Under the direction of control unit 12, acoustic signals of a predetermined frequency, ranging between 50 kHz and 16 MHz, are emitted from the transducer(s) 55 through the surrounding body tissue. The signals reflect off tissue boundaries and are thereafter received back at the transducer, converted into electric signals, and processed by the control unit 12 into viewable images. The images may be viewed on the screen display 26.

Figure 18:
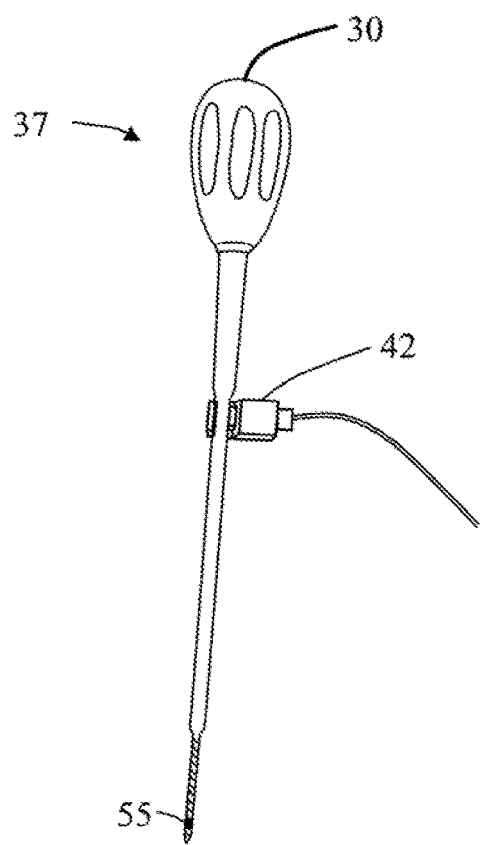
FIG. 18 is side view of a tap member coupled to the system for nerve monitoring via an electric coupling device and incorporating an ultrasound transducer for intraosteal ultrasound imaging according to one aspect of the present invention.
Figure 19:
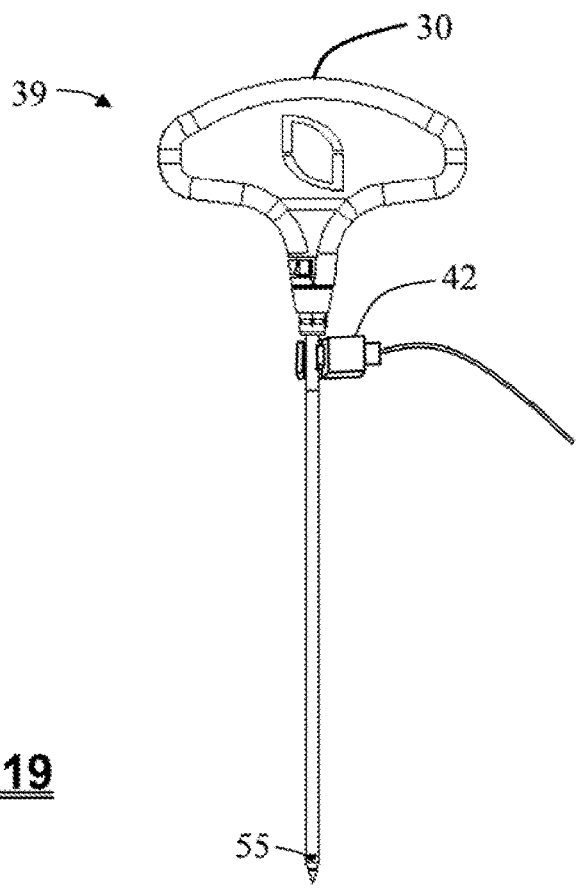
FIG. 19 is side view of a pedicle access probe/bone awl coupled to the system for nerve monitoring via an electric coupling device and incorporating an ultrasound transducer for intraosteal ultrasound imaging according to one aspect of the present invention.

Preferably, at least one transducer is mounted on or within one or more of the surgical accessories 24 (such as screw test probe 30, dilating cannula 38, 40, or retraction assembly 42, shown in FIG. 1) and/or one or more surgical instruments engageable with the system 10 via electric coupling device 58, 68 (such as a tap member 34 or pedicle access probe 32, shown in FIG. 18 and FIG. 19, respectively). As an alternative, a separate transducer (not shown) may be provided and advanced to the surgical target site alone or in conjunction with one or more of the above accessories or instruments, either by advancing alongside or through an interior lumen formed in the instrument for such purpose. Incorporating the transducer 55 onto existing instrumentation permits deployment to the surgical target site during normal operation of the instrument, allowing the advantageous addition of ultrasound imaging without requiring additional steps or instrumentation. It is further contemplated that ultrasound transducers 55 may be deployed at the distal end of various bone screws, including, but not necessarily limited to pedicle screws and/or facet screws, for enabling ultrasound imaging of the surrounding bone during screw implantation.

Figure 20:
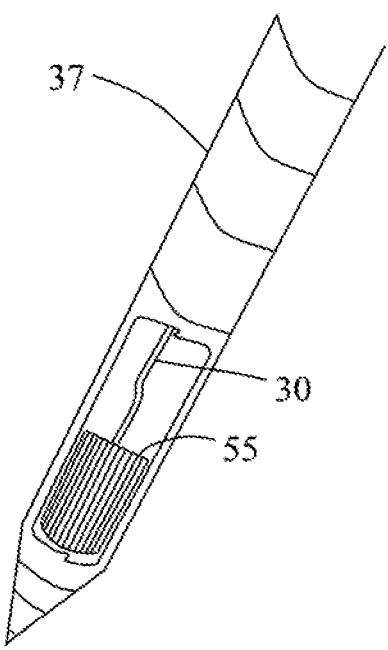
FIG. 20 is a close up side view of the distal end of the tap member of FIG. 18 with a cutaway exposing an integrated ultrasound transducer for use according to one embodiment of the present invention.
Figure 21:
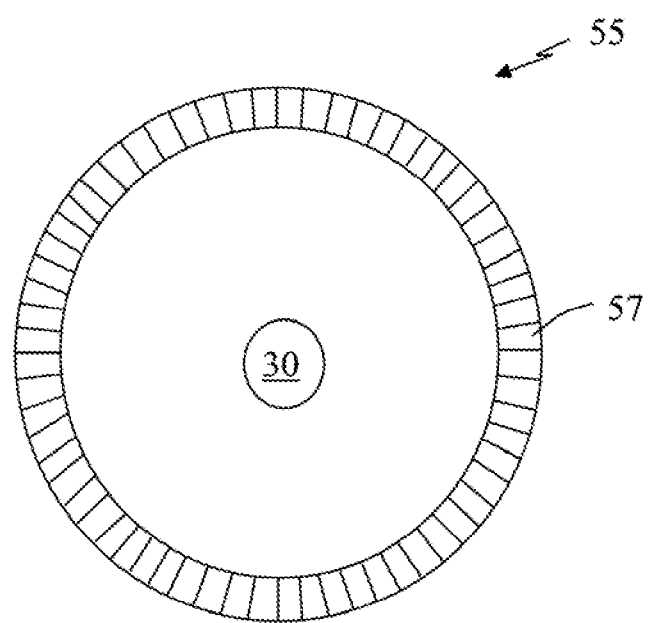
FIG. 21 is an overhead view of one embodiment of a transducer for use according to one embodiment of the present invention, having 64 elements arrayed radially for generating 360 degree images.

For the purposes of example only, FIG. 20 depicts in more detail the incorporation of the ultrasound transducer 55 within tap member 34, according to one exemplary embodiment of the present invention. In the exemplary embodiment, ultrasound transducer 55 is incorporated in the distal end of tap member 34. The transducer 55 may be coupled to the patient module via electric cable, such as by way of example, cable 59. In the pictured embodiment, the surgical system 10 utilizes a 64-element array transducer, such as that available and in use with a number of commercially developed products from Volcano Corp. (Rancho Cordova, Calif.). As best appreciated in FIG. 21, the transducer elements 57 are arrayed in a circular pattern providing for 360° radial imaging of surrounding tissue. Optionally, forward looking transducers may also be employed for additional imaging of tissue lying in front of the surgical instrument. It will be appreciated from the above description that transducer 55 both transmits and receives the acoustic signals. Various other configurations for integrating ultrasound capabilities are also possible. By way of example only, a transducer incorporated in a surgical accessory may transmit acoustic signals to a receiver positioned in the operating room (outside the patients body) and conversely, a transducer positioned in the operating room may transmit acoustic signals to a receiver incorporated into a surgical accessory.

A basic principle underlying the effective use of ultrasound during and/or after pilot hole formation and preparation is the distinctive acoustical characteristics of bone relative to other soft tissues in the body, and more importantly, the varying acoustical characteristics exhibited by bone itself, depending upon its different properties, such as (by way of example only) the type of bone (i.e. cortical or cancellous), bone density, and bone composition. Different acoustical characteristics can include, among others, the velocity, amplitude, and attenuation of sound waves as they pass through tissue. Methods abound in the prior art for quantifying different properties of bone by using ultrasound to determine one or more of its acoustical characteristics and additional methods are known in the prior art for processing ultrasound signals to generate a viewable image of tissue. The present invention makes advantageous use of this information, as well as the general makeup of the bony tissue within the pedicle, to assist surgeons in guidance of surgical instrumentation (including but not limited to tap member 34 and pedicle access probe/awl 36) through the cancellous bone of the interior pedicle and into the vertebral body without breaching the cortical wall.

Figure 22:
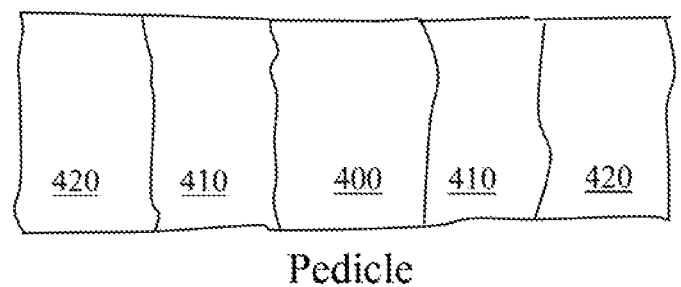
FIG. 22 is an illustration showing the general makeup of various bone regions comprising the spinal pedicle.
Figure 23:
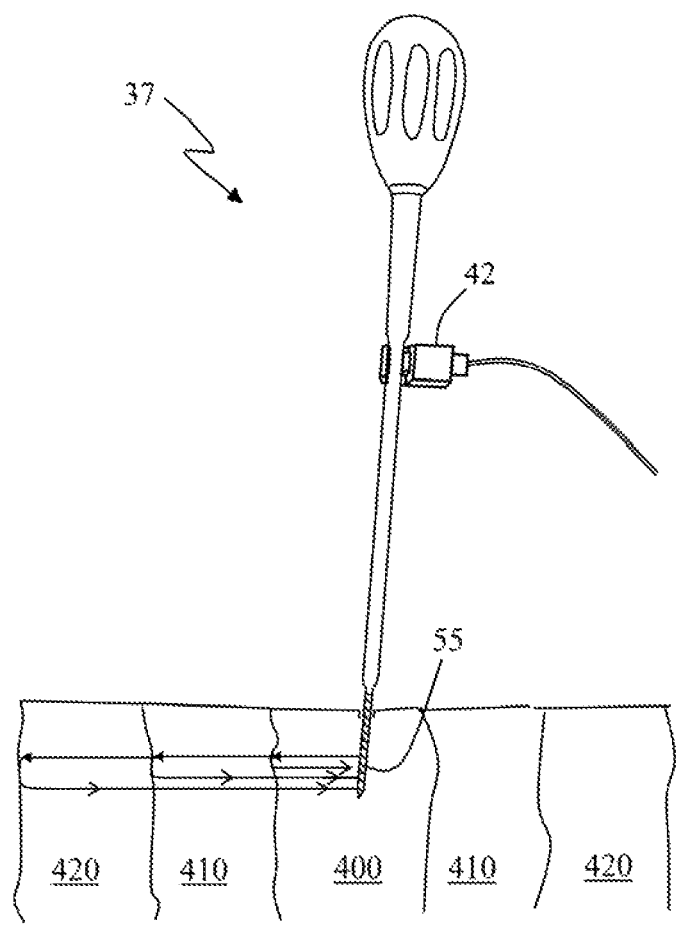
FIG. 23 is an illustration of tap member of FIG. 18 forming a pilot hole along a preferred trajectory utilizing nerve monitoring and ultrasound imaging to maintain the trajectory.
Figure 24:
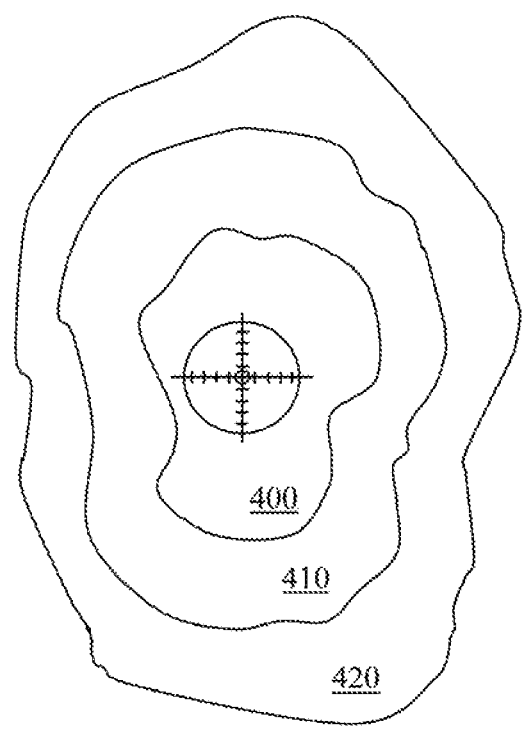
FIG. 24 is a graphical representation of an ultrasound image showing the position of a surgical instrument within the interior pedicle during pedicle integrity testing.

With reference to FIG. 22, the pedicle generally comprises a hard outer region 420 of dense cortical bone and center region 400 of softer, less dense cancellous bone, separated by one or more middle regions 410. The bone in region 410 is generally less dense than outer region 420 but more dense than center region 410. The preferred trajectory for pedicle screw placement is through the soft cancellous bone of the center region 400, thereby avoiding a breach of the pedicle wall. During and/or after pilot hole formation and preparation at least one of the tap member 34, pedicle access probe 36, or screw test probe 30, is advanced through the pedicle. As illustrated in FIG. 23, acoustic signals are emitted from the transducer 55 and travel through the bone. Upon reaching a boundary, a portion of the signal reflects back to the transducer while the remainder of the signal continues moving through the pedicle to the next boundary. The received signals are electronically processed and converted into an image that graphically represents the different tissue, specifically, the different regions of bone 400, 410, and 420. In a preferred embodiment, the ultrasound scan is conducted radially about the surgical instrument thus generating a 360° image of the pedicle relative to the distal end of the surgical instrument, as seen in FIG. 24. From the screen display 46 the surgeon can visually monitor the relative position of the instrument within the pedicle and thus make any necessary adjustments should the instrument position stray from the desired pathway. In another embodiment, the transducer 55 may be substantially located on just one portion of the distal end and the ultrasound scan may be directed by rotating the instrument about its longitudinal axis or any desired portion thereof.

In addition to the image guidance aspect of ultrasound, ultrasound may be used to determine various properties and/or conditions of bone (via any of a number of suitable methods known to the prior art which may be implemented by the system 10) which may also provide useful information. By way of example only, cracks in the pedicle bone, along with their relative position, may be detected using ultrasound. The system 10 may thus detect a breach in the outer wall of the pedicle by ultrasound detection as well as by the nerve monitoring described above. Additional warning indicia such as graphics and/or audible tones may be employed to warn of any danger detected by the system 10 using ultrasound. By way of further example, the system 10 may utilize ultrasound to determine the density of the bone instrument 24 is in contact with. In the event the instrument encounters cortical bone an auditory or visual alert may be initiated thereby providing additional warning of impending breach if the current trajectory is maintained.

Figure 25:
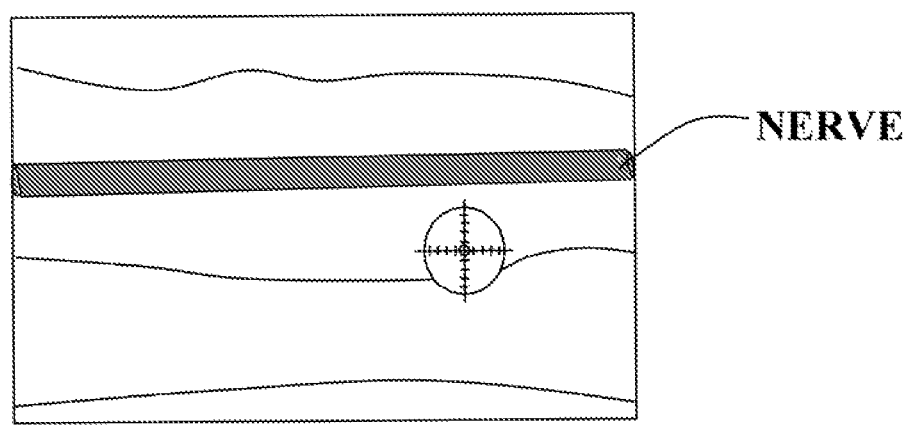
FIG. 25 is a graphical representation of an ultrasound image showing the position of a surgical access component relative to a nerve during nerve detection.

Ultrasound during surgical access may also be used to enhance the nerve detection function described above and proceeds along the same premise as that described for imaging bone. Acoustic signals, generally in the range of 2 MHz-16 MHZ for nerve imaging, are emitted from the transducer 55 located on or within the surgical access components (such as, cannulae 38, 40, and/or retraction assembly 42). The signals reflect of tissue boundaries, such as the interface between fat and muscle or muscle and nerves, and are thereafter received and processed to form a viewable image of the tissue relative to the transducer, which is displayed on screen display 46. Nerves are distinguished from other tissue based on their shape and/or color on the image, as illustrated in FIG. 25. By way of example only, nerves generally appear as round or oval shaped and are generally brighter than the surrounding tissue.

Figure 26:
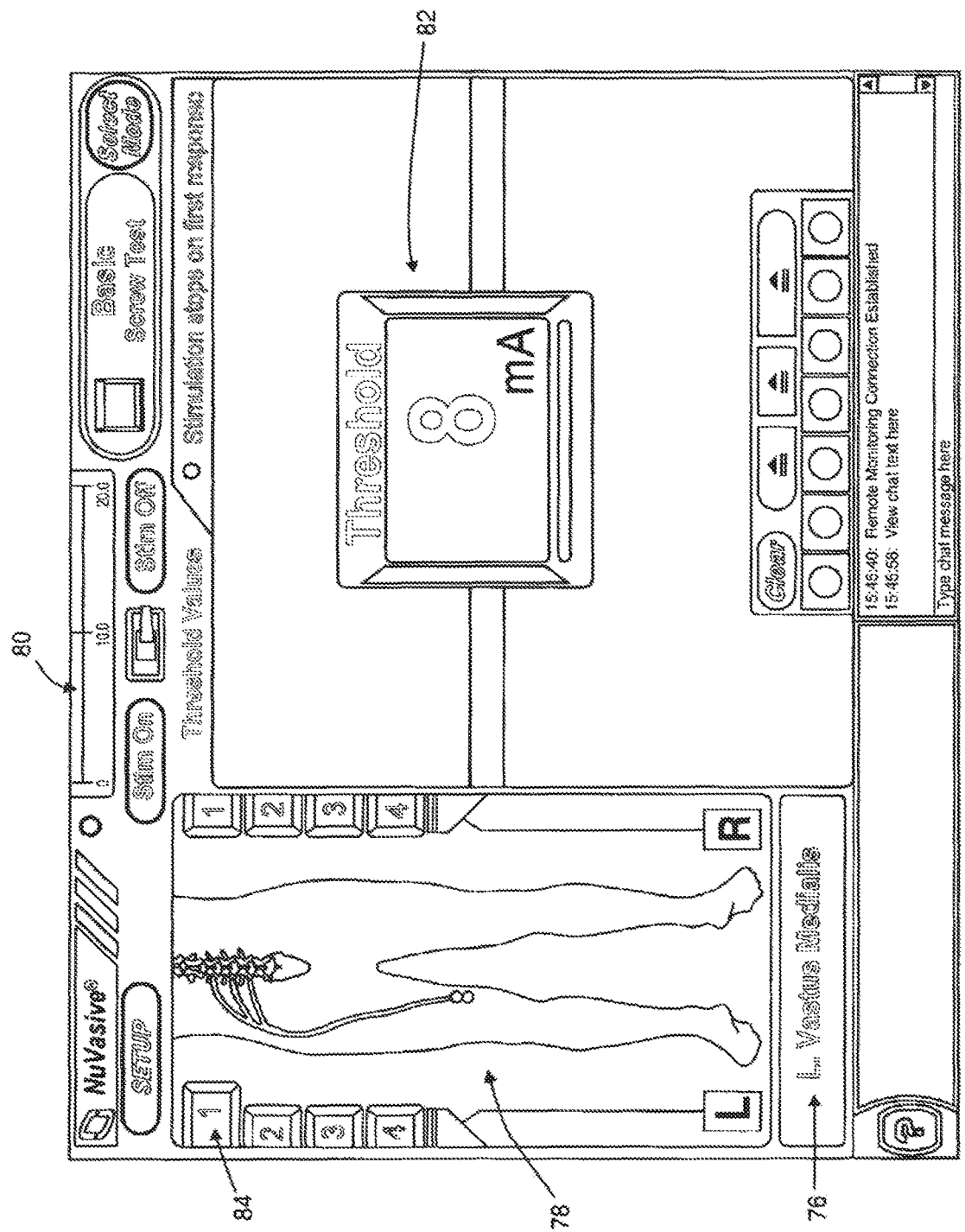
FIG. 26 is an exemplary screen view of the Basic Screw Test mode for performing pedicle integrity assessments with concurrent use of ultrasound according to one embodiment of the present invention.
Figure 27:
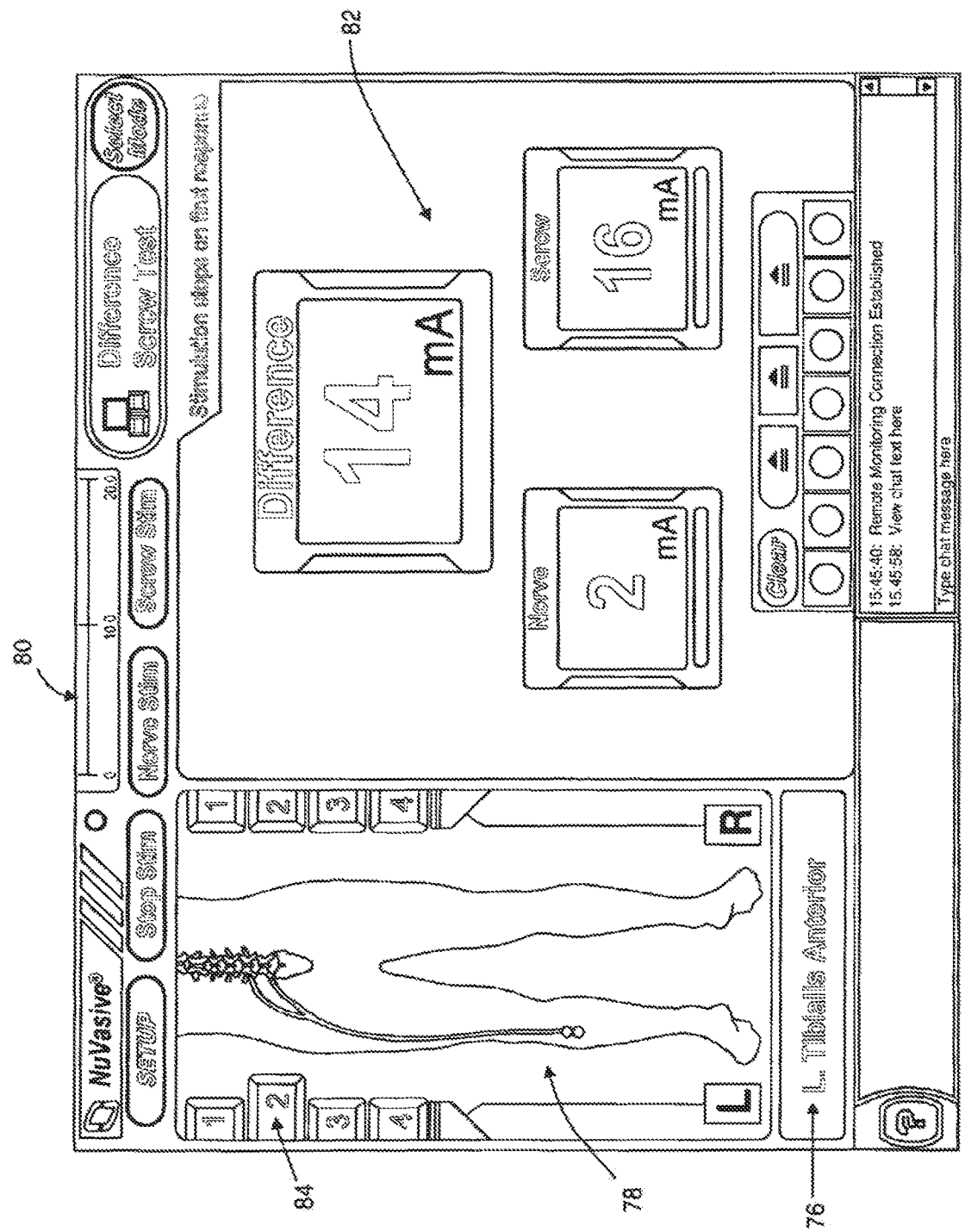
FIG. 27 is an exemplary screen view of the Difference Screw Test mode for performing pedicle integrity assessments with concurrent use of ultrasound according to one embodiment of the present invention.
Figure 28:
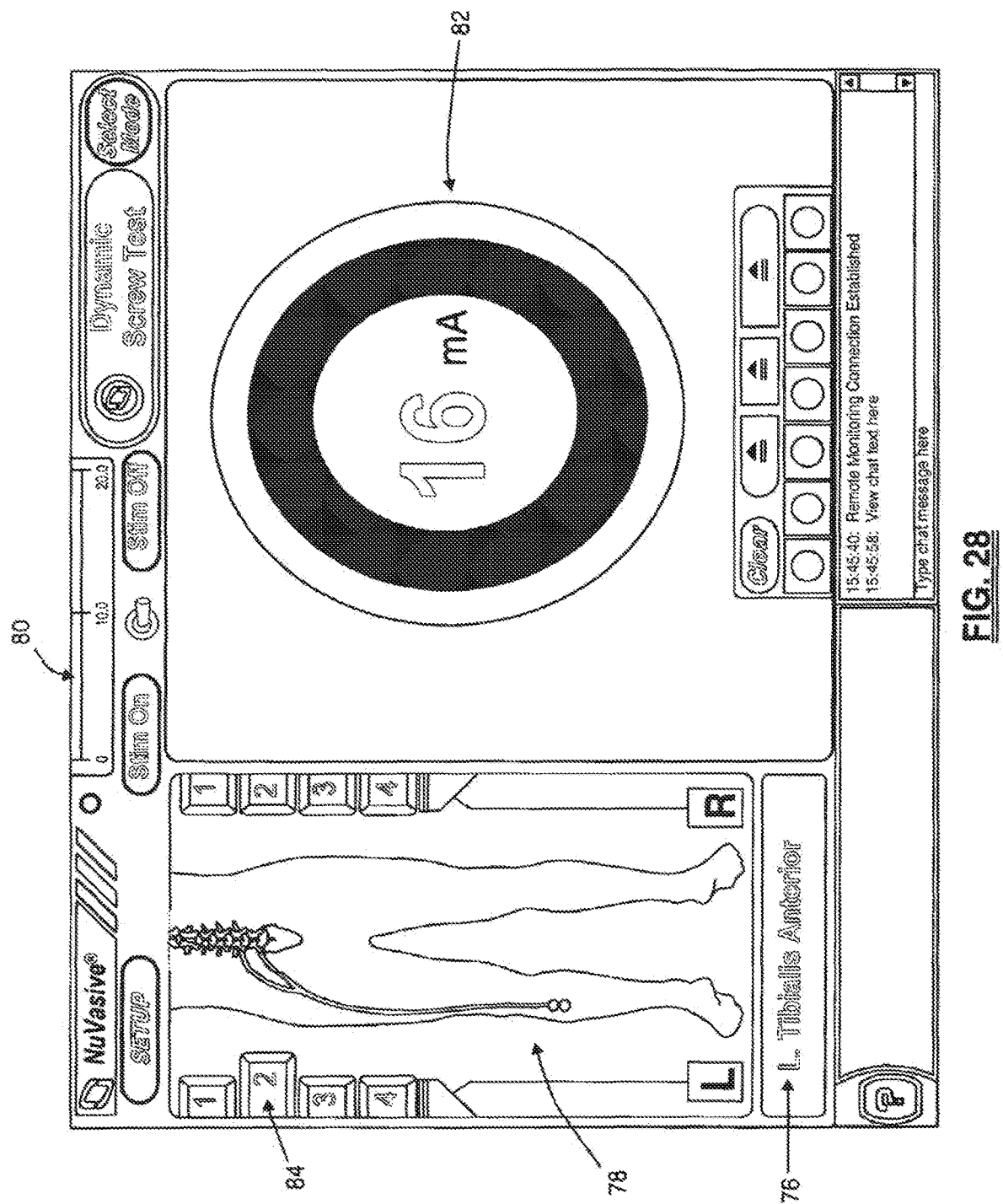
FIG. 28 is an exemplary screen view of the Dynamic Screw Test mode for performing pedicle integrity assessments with concurrent use of ultrasound according to one embodiment of the present invention.
Figure 29:
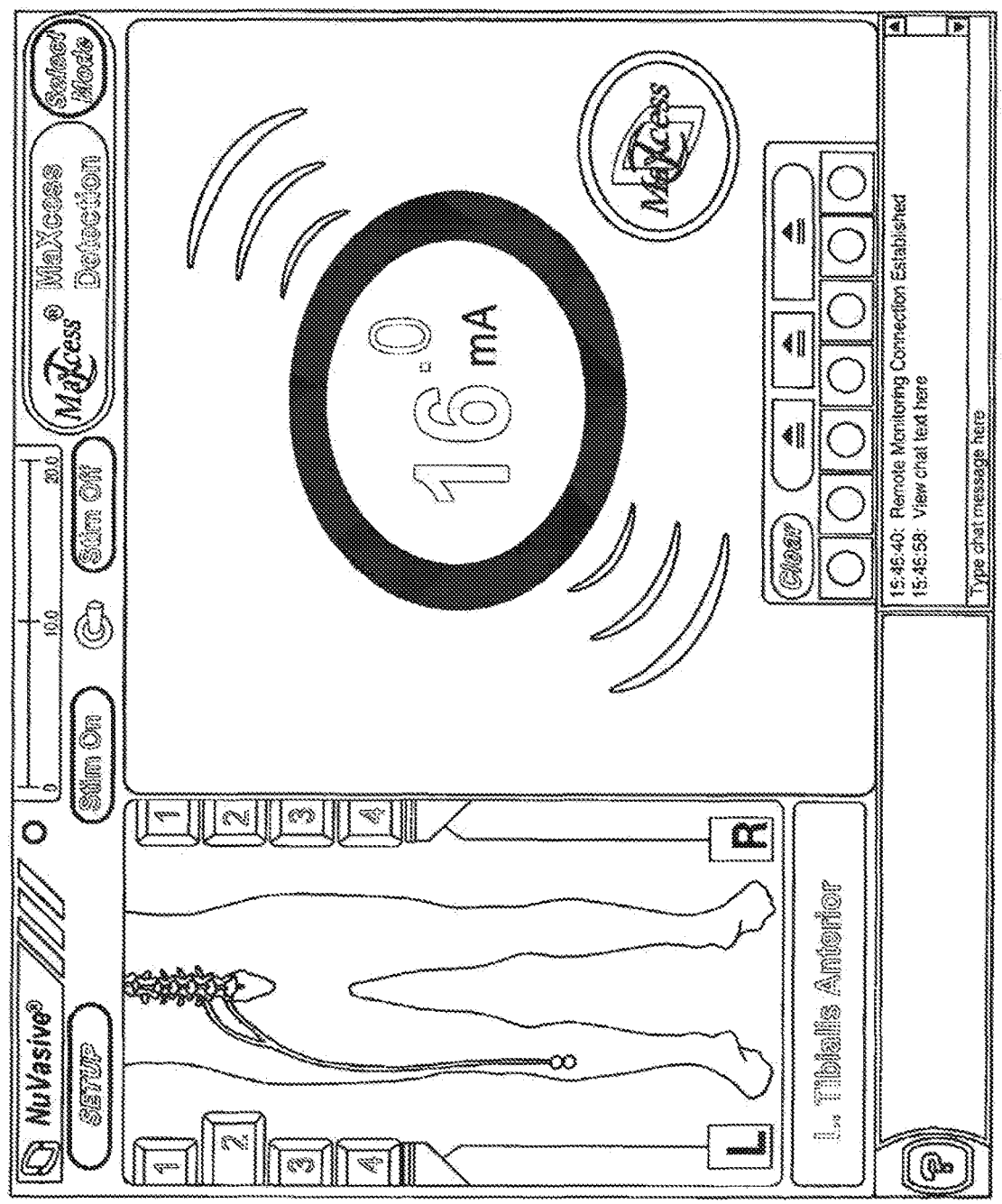
FIG. 29 is an exemplary screen view of the MaXcess Detection mode for detecting nerve presence during spinal access with concurrent use of ultrasound according to one embodiment of the present invention.

Ultrasound may be utilized on system 10 in conjunction with one the neurophysiologic assessment functions, or, it may be used as a stand alone feature. In one embodiment ultrasound is preferably activated from the GUI display 46 by selecting the appropriate command. When ultrasound imaging is utilized in conjunction with nerve monitoring according to the present invention, the ultrasound image is preferably displayed together with the nerve monitoring data thereby allowing the user to receive all the useful information provided by the system 10 at one time without the need to switch between screen views. FIG. 26-28- illustrate, by way of example only, an exemplary screen display for the Basic, Difference, and Dynamic screw test modes, respectively, with the combined ultrasound imaging image 84. In one embodiment, the ultrasound display includes colorized tissue boundaries. The soft cancellous bone 400 may be shown in green representing the preferred instrument positioning. The middle region 410 may be represented in yellow and the cortical bone in red. The distal end of the surgical instrument is represented, by way of example only, as a target finder 430. FIG. 29 illustrates an exemplary screen display of the nerve detection function when ultrasound imaging is in use.

It may also be advantageous for neurophysiologic assessment data and/or ultrasound images captured by the system 10 to be viewable by persons not present in the operating room. It is contemplated that the data and images may be transmitted to one or more remote locations and viewable by authorized persons. This may be accomplished by any number of data transmission methods. In one example, the images may be transmitted to a remote user via remote monitoring software such as that described in detail in the commonly owned and co-pending U.S. patent application Ser. No. 11/418,589, entitled "System and Methods for Performing and Monitoring Neurophysiologic Assessments," filed on May 5, 2006, the entire contents of which are incorporated by reference herein as if set forth in its entirety.

While this invention has been described in terms of a best mode for achieving this invention's objectives, it will be appreciated by those skilled in the art that variations may be accomplished in view of these teachings without deviating from the spirit or scope of the present invention. By way of example the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A method for avoiding nerve tissue during access to a surgical target site at a patient's spine, comprising:
   advancing a distal end of a medical accessory through psoas muscle tissue of the patient to the surgical target site at the patient's spine, wherein the medical accessory is equipped with an ultrasound transducer incorporated into the medical accessory proximate the distal end of the medical accessory, wherein the medical accessory is a dilator; and
   during the advancing of the distal end of the medical accessory through the psoas muscle tissue:
      emitting ultrasound signals with the ultrasound transducer incorporated proximate the distal end of the medical accessory;
      processing the ultrasound signals to identify nerve tissue located proximate the medical accessory;

indicating on a display a position of the ultrasound-identified nerve tissue relative to the medical accessory within the path to the surgical target site, wherein the indicating includes displaying a nerve tissue on the display in a first color or first shade of color distinct from a second color or second shade of color used to designate surrounding tissue; and adjusting a path of the medical accessory to the surgical target site to avoid nerve tissue positioned within the path to the surgical target site identified by the processing of the ultrasound signals emitted by the medical accessory.

2. The method of claim 1, wherein the surgical target site is an intervertebral disc or a vertebral body.

3. The method of claim 1, further comprising:
processing ultrasound signal data into viewable images for viewing on the display.

4. The method of claim 1, wherein the emitting of the ultrasound signals includes emitting the ultrasound signals circumferentially about the distal end of the medical accessory.

5. The method of claim 1, further comprising: modifying a direction of the emitted ultrasound signals by rotating the medical accessory while advancing the medical accessory through the psoas muscle tissue to the surgical target site.

6. The method of claim 1, further comprising:
receiving the ultrasound signals after the ultrasound signals reflect off the nerve tissue or vasculature proximate the medical accessory.

7. The method of claim 1, further comprising:
detecting the emitted ultrasound signals at a receiver positioned outside of the patient's body.

8. A method for guiding surgical instrumentation through anatomy of a subject, the method comprising:
creating a surgical access corridor, wherein creating the surgical access corridor includes:
advancing a dilator along a lateral, trans-psoas path from an incision site through non-bone soft tissue to a surgical target site at a spine, wherein the dilator includes an ultrasound transducer; and
while creating the surgical access corridor:
emitting ultrasound signals proximate the dilator;
processing the ultrasound signals to identify nerve tissue located proximate the dilator;
indicating on a display a position of the nerve tissue relative to the dilator, wherein the indicating includes displaying nerve tissue on the display in a first color or first shade of color distinct from a second color or second shade of color used to designate surrounding tissue; and
adjusting a path of the dilator to the surgical target site to avoid nerve tissue located proximate the dilator identified by the processing of the ultrasound signals emitted by the medical accessory.

9. The method of claim 8, further comprising:
while creating the surgical access corridor, processing ultrasound signal data into viewable images for viewing on the display.

10. The method of claim 8, wherein the emitting of the ultrasound signals includes emitting the ultrasound signals circumferentially about a distal end of the dilator.

11. The method of claim 8, further comprising:
modifying a direction of the emitted ultrasound signals by rotating the dilator about a longitudinal axis of the dilator while advancing the dilator through the non-bone soft tissue to the surgical target site.

12. The method of claim 8, further comprising:
receiving the ultrasound signals at a receiver of the dilator after the ultrasound signals reflect off of the nerve tissue or vasculature proximate the dilator.

13. A method comprising:
while a distal end of a medical accessory is being advanced through psoas muscle tissue of a patient:
emitting ultrasound signals with an ultrasound transducer incorporated with the medical accessory proximate the distal end of the medical accessory;
processing the ultrasound signals to monitor for nerve tissue and vasculature located proximate the medical accessory;
emitting an electrical stimulation signal from an electrode of the medical accessory disposed proximate the distal end of the medical accessory, the electrical stimulation signal configured to evoke muscle activity;
detecting muscle activity evoked by the electrical stimulation signal;
processing the muscle activity to monitor for nerve tissue;
indicating on a display a position of the nerve tissue and vasculature relative to the medical accessory based on the processed ultrasound signals and the processed neuromuscular response, wherein the indicating includes displaying nerve tissue on the display in a first color or first shade of color distinct from a second color or second shade of color used to designate surrounding tissue; and
adjusting a path of the dilator to the surgical target site to avoid nerve tissue located proximate the dilator identified by the processing of the ultrasound signals emitted by the medical accessory.

14. The method of claim 13, further comprising:
simultaneously providing at the display:
an ultrasound image based on the processed ultrasound signals; and
nerve monitoring data based on the muscle activity.

15. The method of claim 13, wherein the medical accessory is a retractor.

* * * * *